US011806319B2

(12) United States Patent
Wilkhu et al.

(10) Patent No.: US 11,806,319 B2
(45) Date of Patent: Nov. 7, 2023

(54) PHARMACEUTICAL COMPOSITION COMPRISING A CANNABINOID

(71) Applicant: GW Research Limited, Cambridge (GB)

(72) Inventors: Jitinder Wilkhu, Cambridge (GB); Johan Bender, Berg en Dal (NL)

(73) Assignee: GW Research Limited, Cambridge (GB)

( * ) Notice: Subject to any disclaimer, the term of this patent is extended or adjusted under 35 U.S.C. 154(b) by 444 days.

(21) Appl. No.: 16/959,350

(22) PCT Filed: Jan. 2, 2019

(86) PCT No.: PCT/GB2019/050007
§ 371 (c)(1),
(2) Date: Jun. 30, 2020

(87) PCT Pub. No.: WO2019/135075
PCT Pub. Date: Jul. 11, 2019

(65) Prior Publication Data
US 2021/0059960 A1     Mar. 4, 2021

(30) Foreign Application Priority Data
Jan. 3, 2018   (GB) ..................... 1800072

(51) Int. Cl.
A61K 31/05      (2006.01)
A61K 31/352     (2006.01)
A61K 47/10      (2017.01)
A61K 47/12      (2006.01)
A61K 47/22      (2006.01)
A61K 47/34      (2017.01)

(52) U.S. Cl.
CPC .......... A61K 31/05 (2013.01); A61K 31/352 (2013.01); A61K 47/10 (2013.01); A61K 47/12 (2013.01); A61K 47/22 (2013.01); A61K 47/34 (2013.01)

(58) Field of Classification Search
CPC ...... A61K 31/05; A61K 31/352; A61K 47/10; A61K 47/12; A61K 47/22; A61K 47/34
See application file for complete search history.

(56) References Cited

U.S. PATENT DOCUMENTS

| | | | |
|---|---|---|---|
| 6,294,192 B1 | 9/2001 | Patel et al. | |
| 6,403,126 B1 | 6/2002 | Webster | |
| 6,949,582 B1 | 9/2005 | Wallace | |
| 8,293,786 B2 | 10/2012 | Stinchcomb | |
| 8,673,368 B2 | 3/2014 | Guy et al. | |
| 9,017,737 B2 | 4/2015 | Kikuchi et al. | |
| 9,023,322 B2 | 5/2015 | Van Damme et al. | |
| 9,066,920 B2 | 6/2015 | Whalley et al. | |
| 9,125,859 B2 | 9/2015 | Whalley et al. | |
| 9,095,554 B2 | 10/2015 | Lewis et al. | |
| 9,168,278 B2 | 10/2015 | Guy et al. | |
| 9,259,449 B2 | 2/2016 | Raderman | |
| 9,345,771 B2 * | 5/2016 | Goskonda | A61K 9/0095 |
| 9,474,726 B2 | 10/2016 | Guy et al. | |
| 9,522,123 B2 | 12/2016 | Whalley et al. | |
| 9,730,911 B2 | 8/2017 | Verzura et al. | |
| 9,949,936 B2 | 4/2018 | Guy et al. | |
| 9,949,937 B2 | 4/2018 | Guy et al. | |
| 9,956,183 B2 | 5/2018 | Guy et al. | |
| 9,956,184 B2 | 5/2018 | Guy et al. | |
| 9,956,185 B2 | 5/2018 | Guy et al. | |
| 9,956,186 B2 | 5/2018 | Guy et al. | |
| 10,092,525 B2 | 10/2018 | Guy et al. | |
| 10,111,840 B2 | 10/2018 | Guy et al. | |
| 10,137,095 B2 | 11/2018 | Guy et al. | |
| 10,441,617 B2 * | 10/2019 | Lewis | A01H 5/10 |
| 10,583,096 B2 | 3/2020 | Guy et al. | |
| 10,603,288 B2 | 3/2020 | Guy et al. | |
| 10,709,671 B2 | 7/2020 | Guy et al. | |
| 10,709,673 B2 | 7/2020 | Guy et al. | |
| 10,709,674 B2 | 7/2020 | Guy et al. | |
| 10,765,643 B2 | 9/2020 | Guy et al. | |
| 10,807,777 B2 | 10/2020 | Whittle | |
| 10,849,860 B2 | 12/2020 | Guy et al. | |
| 10,918,608 B2 | 2/2021 | Guy et al. | |
| 10,966,939 B2 | 4/2021 | Guy et al. | |
| 11,065,209 B2 | 7/2021 | Guy et al. | |
| 11,065,227 B2 | 7/2021 | Stott et al. | |
| 11,096,905 B2 | 8/2021 | Guy et al. | |
| 11,147,776 B2 | 10/2021 | Stott et al. | |

(Continued)

FOREIGN PATENT DOCUMENTS

AU    2016203127 A1    5/2012
CA      2737447 A1    10/2012
(Continued)

OTHER PUBLICATIONS

[No Author Listed], Cannabinoid. Wikipedia. Retrieved on Jul. 9, 2015 from https://en.wikipedia.org/wiki/Cannabinoid, 15 pages.
Appendino, J.P. et al., "Position Statement on the Use of Medical Cannabis for the Treatement of Epilepsy in Canada," Can J. Neurol. Sci., 33:783-786 (2006).
AU Re-examination report—standard patent for Australian Patent No. 2012204800, dated May 3, 2019.
Astruc-Diaz, F., "Cannabinoids delivery systems based on supramolecular inclusion complexes and polymeric nanocapsules for treatment of neuropathic pain," Université Claude Bernard—Lyon I, 2012, submitted on Jan. 23, 2014; https://tel.archives-ouvertes.fr/tel-00935588 [accessed Nov. 1, 2019].
BASF Pharma Ingredients Lutrol® F68 NF [online]. Retrieved on Feb. 22, 2022 from: http://www2.basf.us/Pharma/pdf/Lutrol_F_68.pdf, 2001, 1 page.

(Continued)

Primary Examiner — Sahar Javanmard
(74) Attorney, Agent, or Firm — COOLEY LLP

(57) ABSTRACT

The present invention relates to a novel cannabinoid oral pharmaceutical dosage form, based on a Type IV or Type IV-like formulation, as classified using the Lipid Formulation Classification System. The formulation is contained in a container. By Type IV-like, it is meant that the formulation comprises no oil, for example no triglycerides or mixed glycerides.

18 Claims, 1 Drawing Sheet

(56) References Cited

U.S. PATENT DOCUMENTS

| | | |
|---|---|---|
| 11,147,783 B2 | 10/2021 | Stott et al. |
| 11,154,516 B2 | 10/2021 | Guy et al. |
| 11,154,517 B2 | 10/2021 | Wright et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,229,612 B2 | 1/2022 | Wright et al. |
| 11,291,631 B2 | 4/2022 | Shah |
| 11,311,498 B2 | 4/2022 | Guy et al. |
| 11,357,741 B2 | 6/2022 | Guy et al. |
| 11,400,055 B2 | 8/2022 | Guy et al. |
| 11,406,623 B2 | 8/2022 | Guy et al. |
| 11,419,829 B2 | 8/2022 | Whalley et al. |
| 11,426,362 B2 | 8/2022 | Wright et al. |
| 2004/0049059 A1 | 3/2004 | Mueller |
| 2004/0110828 A1 | 6/2004 | Chowdhury et al. |
| 2004/0228921 A1 | 11/2004 | Chowdhury et al. |
| 2005/0042172 A1 | 2/2005 | Whittle |
| 2005/0266108 A1 | 12/2005 | Flockhart et al. |
| 2006/0039959 A1 | 2/2006 | Wessling |
| 2007/0060638 A1 | 3/2007 | Olmstead |
| 2007/0060639 A1 | 3/2007 | Wermeling |
| 2008/0119544 A1 | 5/2008 | Guy et al. |
| 2008/0188461 A1 | 8/2008 | Guan |
| 2008/0279940 A1 | 11/2008 | Rigassi et al. |
| 2009/0035368 A1 | 2/2009 | Moschwitzer |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0231083 A1 | 9/2012 | Carley et al. |
| 2012/0270845 A1 | 10/2012 | Bannister |
| 2013/0089600 A1 | 4/2013 | Winnicki |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0110828 A1 | 4/2014 | Otremba et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0250733 A1 | 9/2015 | Odidi |
| 2015/0320698 A1 | 11/2015 | Whalley et al. |
| 2015/0335590 A1 | 11/2015 | Whalley et al. |
| 2015/0342902 A1 | 12/2015 | Vangara et al. |
| 2015/0343071 A1 | 12/2015 | Vangara |
| 2015/0359755 A1 | 12/2015 | Guy et al. |
| 2015/0359756 A1 | 12/2015 | Guy et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0184258 A1 | 6/2016 | Murty et al. |
| 2016/0213624 A1 | 7/2016 | Lindeman |
| 2016/0220529 A1 | 8/2016 | Guy et al. |
| 2016/0256411 A1 | 9/2016 | Aung-Din |
| 2016/0271252 A1 | 9/2016 | Vangara et al. |
| 2016/0346235 A1 | 12/2016 | Singh et al. |
| 2016/0367496 A1 | 12/2016 | Vangara et al. |
| 2017/0007551 A1 | 1/2017 | Guy et al. |
| 2017/0119660 A1 | 5/2017 | Temtsin-Krayz et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0224634 A1 | 8/2017 | Vangara et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Wilkhu et al. |
| 2018/0028489 A1 | 2/2018 | Vangara et al. |
| 2018/0071210 A1 | 3/2018 | Wilkhu et al. |
| 2018/0228751 A1 | 8/2018 | Stott et al. |
| 2018/0289665 A1 | 10/2018 | Turner et al. |
| 2018/0338931 A1 | 11/2018 | Guy et al. |
| 2019/0083418 A1 | 3/2019 | Guy et al. |
| 2019/0167583 A1 | 6/2019 | Shah et al. |
| 2019/0175547 A1 | 6/2019 | Stott et al. |
| 2019/0240160 A1 | 8/2019 | He et al. |
| 2019/0314296 A1 | 10/2019 | Wright et al. |
| 2019/0321307 A1 | 10/2019 | Guy et al. |
| 2020/0138738 A1 | 5/2020 | Guy et al. |
| 2020/0206153 A1 | 7/2020 | Whalley et al. |
| 2020/0237683 A1 | 7/2020 | Whalley et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0169824 A1 | 6/2021 | Guy et al. |
| 2021/0177773 A1 | 6/2021 | Guy et al. |
| 2021/0290565 A1 | 9/2021 | Guy et al. |
| 2021/0330636 A1 | 10/2021 | Guy et al. |
| 2021/0330797 A1 | 10/2021 | Vangara et al. |
| 2021/0401771 A1 | 12/2021 | Guy et al. |
| 2022/0000800 A1 | 1/2022 | Guy et al. |
| 2022/0008355 A1 | 1/2022 | Guy et al. |
| 2022/0016048 A1 | 1/2022 | Guy et al. |
| 2022/0023232 A1 | 1/2022 | Guy et al. |
| 2022/0040155 A1 | 2/2022 | Guy et al. |
| 2022/0062197 A1 | 3/2022 | Stott et al. |
| 2022/0062211 A1 | 3/2022 | Stott et al. |
| 2022/0087951 A1 | 3/2022 | Guy et al. |
| 2022/0096397 A1 | 3/2022 | Wright et al. |
| 2022/0168266 A1 | 6/2022 | Guy et al. |
| 2022/0183997 A1 | 6/2022 | Guy et al. |
| 2022/0184000 A1 | 6/2022 | Guy et al. |
| 2022/0202738 A1 | 6/2022 | Guy et al. |
| 2022/0211629 A1 | 7/2022 | Wilkhu et al. |
| 2022/0233495 A1 | 7/2022 | Silcock et al. |
| 2022/0249396 A1 | 8/2022 | Guy et al. |
| 2022/0257529 A1 | 8/2022 | Guy et al. |

FOREIGN PATENT DOCUMENTS

| | | |
|---|---|---|
| CA | 2859934 A1 | 3/2016 |
| CN | 101040855 A | 9/2007 |
| CN | 103110582 A | 5/2013 |
| CN | 104840967 A | 8/2015 |
| DE | 102012-105063 | 12/2013 |
| EP | 2448637 B1 | 5/2012 |
| EP | 2 741 750 A1 | 6/2014 |
| GB | 2384707 A | 8/2003 |
| GB | 2434097 A | 7/2007 |
| GB | 2434312 A | 7/2007 |
| GB | 2450753 A | 1/2009 |
| GB | 2456183 A | 7/2009 |
| GB | 2471523 A | 1/2011 |
| GB | 2478595 A | 9/2011 |
| GB | 2479153 A | 10/2011 |
| GB | 2471565 B | 7/2012 |
| GB | 2478072 B | 12/2012 |
| GB | 2478074 B | 12/2012 |
| GB | 2492487 A | 1/2013 |
| GB | 2487712 B | 10/2015 |
| GB | 2531282 A | 4/2016 |
| GB | 2539472 A | 12/2016 |
| GB | 2438682 B | 12/2017 |
| GB | 2556960 A | 6/2018 |
| JP | 2010-270110 A | 12/2010 |
| WO | WO 01/28590 A2 | 4/2001 |
| WO | WO 02/064109 A2 | 8/2002 |
| WO | WO 03/099302 A1 | 12/2003 |

(56) References Cited

FOREIGN PATENT DOCUMENTS

| | | |
|---|---|---|
| WO | WO 04/016246 A1 | 2/2004 |
| WO | WO 04/016277 A2 | 2/2004 |
| WO | WO 2006/054057 A2 | 5/2006 |
| WO | WO 2006/133941 A2 | 12/2006 |
| WO | WO 2007/032962 A2 | 3/2007 |
| WO | WO 2007/083098 A1 | 7/2007 |
| WO | WO 2007/138322 A1 | 12/2007 |
| WO | WO 2008/019146 A2 | 2/2008 |
| WO | WO 2008/021394 A2 | 2/2008 |
| WO | WO 2008/024490 A2 | 2/2008 |
| WO | WO 2008/094181 A3 | 8/2008 |
| WO | WO 2008/129258 A1 | 10/2008 |
| WO | WO 2008/144475 A1 | 11/2008 |
| WO | WO 2008/146006 A1 | 12/2008 |
| WO | WO 2009/007697 A1 | 1/2009 |
| WO | WO 2009/007698 A1 | 1/2009 |
| WO | WO 2009/020666 A1 | 12/2009 |
| WO | WO 2010/012506 A1 | 2/2010 |
| WO | WO 2011/001169 A1 | 1/2011 |
| WO | WO 2011/002285 A1 | 1/2011 |
| WO | WO 2011/121351 A1 | 10/2011 |
| WO | WO 2012/033478 A1 | 3/2012 |
| WO | WO 2012/093255 A1 | 7/2012 |
| WO | WO 2013/024373 A1 | 2/2013 |
| WO | WO 2013/032351 A1 | 3/2013 |
| WO | WO 2014/146699 A1 | 9/2014 |
| WO | WO 2015/142501 A1 | 9/2015 |
| WO | WO 2015/184127 A2 | 12/2015 |
| WO | WO 2015/193667 A1 | 12/2015 |
| WO | WO 2015/193668 A1 | 12/2015 |
| WO | WO 2016/022936 A1 | 2/2016 |
| WO | WO 2016/059405 A1 | 4/2016 |
| WO | WO 2016/084075 A1 | 6/2016 |
| WO | WO 2016/118391 A1 | 7/2016 |
| WO | WO 2016/141056 A1 | 9/2016 |
| WO | WO 2016/147186 A1 | 9/2016 |
| WO | WO 2016/199148 A1 | 12/2016 |
| WO | WO 2017/059859 A1 | 4/2017 |
| WO | WO 2017/072774 A1 | 5/2017 |
| WO | WO 2017/168138 A1 | 10/2017 |
| WO | WO 2018/002636 A1 | 1/2018 |
| WO | WO 2018/002637 A1 | 1/2018 |
| WO | WO 2018/002665 A1 | 1/2018 |
| WO | WO 2018/035030 A1 | 2/2018 |
| WO | WO 2018/037203 A1 | 3/2018 |
| WO | WO 2019/082171 A1 | 5/2019 |
| WO | WO 2019/135075 A1 | 7/2019 |
| WO | WO 2019/135076 A1 | 7/2019 |
| WO | WO 2019/135077 A1 | 7/2019 |
| WO | WO 2019/159174 A1 | 8/2019 |
| WO | WO 2020/240184 A1 | 12/2020 |

OTHER PUBLICATIONS

Benowitz & Jones, "Cardiovascular and metabolic considerations in prolonged cannabinoid administration in man," J Clin Pharm, 21:214S-223S (1981).
Chiu, P. et al., "The influence of delta9-tetrahydrocannabinol, cannabinol and cannabidiol on tissue oxygen consumption," Res Commun 12, No. 2, pp. 267-286, 1977.
Devinsky, Orrin, M.D. of the Department of Neurology for NYU Langone School of Medicine presents his talk on "Cannabidiols: A Brief History," at NYU School of Medicine's Cannabidiol Conference (Oct. 4, 2013). Video published online. <http://faces.med.nyu.edu/research-education/cannabidiol-conference>, 16 pages.
Devinsky et al., "Trial of Cannabidiol for Drug-Resistant Seizures in the Dravet Syndrome," N Engl J Med, 376(21):2011-2020 (2017).
Geede et al., "3.330: Whole Cannabis Extract of High Concentration Cannabidiol May Calm Seizures in Highly Refractory Pediatric Epilepsies," American Epilepsy Society, Dec. 2013, 449-450.
Hempel, B. J. et al., "An assessment of sex differences in Δ9-tetrahydrocannabinol (THC) taste and place conditioning," Pharmacology, Biochemistry, and Behavior, 153:69-75 (2017).
Hill et al., "Cannabidivarin in anticonvulsant in mouse and rat," Br J Pharmacol, 167(8):1629-1642 (2012).
International Search Report and Written Opinion dated Oct. 25, 2016 for International Application No. PCT/GB2016/052340, 12 pages.
Jones et al., "Cannabidiol Displays Antiepileptiform and Antiseizure Properties in Vitro and in Vivo," J Pharmacol Exp Ther., 332(2):559-577 (2010).
Lazzari, P. et al., "Antinociceptive activity of Δ9-tetrahydrocannabinol non-ionic microemulsions," International Jounral of Pharmaceutics, 393:238-243 (210).
Manni et al., "Obstructive Sleep Apnea in a Clinical Series of Adult Epilepsy Patients: Frequency and Features of the Comorbidity," Epilepsia, 44(6):836-840 (2003).
McCormick et al., "On the cellular and network bases of epileptic seizures," Annu Rev Physiol., 63:815-846 (2001).
Medicos [online]. "Convulsive Disorders and their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving>, 3 pages.
Monteagudo, E. et al., "Pharmaceutical optimization of lipid-based dosage forms for the improvement of taste-masking, chemical stability and solubilizing capacity pf phenobarbital," Drug Development and Industrial Pharmacy, 40(6):783-792 (2014).
Moral et al., "Pipeline on the Move," Drugs of the Future, 39(1):49-56 (2014).
Porter et al., "Report of a parent survey of cannabidiol-enriched cannabis use in pediatric treatment-resistant epilepsy," Epilepsy Behav. Dec. 2013;29(3):574-7.
Potter, "Cannabis Horticulture," Chapter 4, Handbook of Cannabis, ed. Roger G. Pertwee, pp. 65-88 (2014).
SalutarisDrops.com [online], "Cannabidiol for Aicardi Syndrome," Salutaris, available on or before Oct. 2014, retrieved on Feb. 10, 2017, URL <http://web.archive.org/web/20141012220050/http://salutarisdrops.com/cannabidiol-aicardi-syndrome/>, 3 pages.
U.S. Department of Health and Human Services, Food and Drug Administration Center for Drug Evaluation and Research (CDER), "Guidance for Industry Estimating the Maximun Safe Starting Dose in Initial Clinical Trials for Therapeutics in Adult Healthy Volunteers," Jul. 2005, 30 pages.
U.S. Appl. No. 15/640,033, filed Jun. 30, 2017.
U.S. Appl. No. 16/467,639, filed Jun. 7, 2019.
U.S. Appl. No. 16/624,106, filed Dec. 18, 2019.
U.S. Appl. No. 16/737,707, filed Jan. 8, 2020.
U.S. Appl. No. 16/764,701, filed May 15, 2020.
U.S. Appl. No. 16/768,241, filed May 29, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 17/025,130, filed Sep. 18, 2020.
U.S. Appl. No. 17/050,956, filed Oct. 27, 2020.
U.S. Appl. No. 16/935,005, filed Jul. 21, 2020.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/470,382, filed Sep. 9, 2021.
U.S. Appl. No. 17/472,000, filed Sep. 10, 2021.
U.S. Appl. No. 17/472,016, filed Sep. 10, 2021.
U.S. Appl. No. 17/548,232, filed Dec. 10, 2021.
U.S. Appl. No. 17/477,172, filed Sep. 16, 2021.
U.S. Appl. No. 17/606,370, filed Oct. 25, 2021.
U.S. Appl. No. 17/611,824, filed Nov. 16, 2021.
U.S. Appl. No. 17/529,005, filed Nov. 17, 2021.
U.S. Appl. No. 17/615,422, filed Nov. 30, 2021.
U.S. Appl. No. 17/552,487, filed Dec. 16, 2021.
U.S. Appl. No. 17/627,946, filed Jan. 18, 2022.
U.S. Appl. No. 17/631,069, filed Jan. 28, 2022.

(56) References Cited

OTHER PUBLICATIONS

U.S. Appl. No. 17/638,629, filed Feb. 25, 2022.
U.S. Appl. No. 17/689,607, filed Mar. 8, 2022.
U.S. Appl. No. 17/689,245, filed Mar. 8, 2022.
U.S. Appl. No. 17/744,224, filed May 13, 2022.
U.S. Appl. No. 17/705,443, filed Mar. 28, 2022.
U.S. Appl. No. 17/680,048, filed Apr. 11, 2022.
U.S. Appl. No. 17/770,435, filed Apr. 20, 2022.
U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.
U.S. Appl. No. 17/743,653, filed May 13, 2022.
U.S. Appl. No. 17/777,734, filed May 18, 2022.
U.S. Appl. No. 17/777,677, filed May 18, 2022.
U.S. Appl. No. 17/777,681, filed May 18, 2022.
U.S. Appl. No. 17/786,949, filed Jun. 17, 2022.
U.S. Appl. No. 17/819,046, filed Aug. 11, 2022.
[No Author Listed] "Cannabidiol Therapy for Aicardi Syndrome" Aug. 2014.
No Author Listed], Cover and Table of Contents, J Pharmacology and Exp Therapeutics, Feb. 2010, 332(2), 4 pages.
Alger. "Not too excited? Thank your endocannabinoids." Neuron. Aug. 17, 2006;51(4):393-5.
Ames et al. "Anticonvulsant effect of cannabidiol." S Afr Med J. Jan. 4, 1986;69(1): 14.
American Epilepsy Society, Three Studies Shed New Light on the Effectivemess of Cannabis in Epilepsy, Oct. 14, 2014.
Arain et al. "Pregabalin in the management of partial epilepsy." Neuropsychiatr Dis Treat. 2009;5:407-13. Epub Aug. 20, 2009.
Arslan and Timaksiz. "Self-emulsifying Drug Delivery Systems," F ABAD J Pharm Sci, 2013 38( 1):55-64.
Arzimanoglou et al. "All children who experience epileptic falls do not necessarily have Lennox-Gastaut syndrome . . . but many do," Epileptic Discord, 2011, 13:S3-S13.
AU Third Party Observations for Application No. AU2012314129, dated Mar. 19, 2015, 51 pages.
Avoli et al. "Cellular and molecular mechanisms of epilepsy in the human brain." Prog Neurobiol. Oct. 2005;77(3):166-200.
Bakhsh, Miftaah-al-Khazaain. 1930: 607-8. Urdu. Exhibit 3.
Bancaud et al. "Proposal for Revised Clinical and Electroencephalographic Classification of Epileptic Seizures." Epilepsia. Aug. 1981;22(4):489-501.
Barker-Haliski et al. "How Clinical Development Can, and Should. Inform Translational Science," Neuron, Nov. 2014, 84: 582-593.
Banerjee et al. "Case Report: Aicardi syndrome: A report of five Indian cases," Neurology India,Mar. 2006, 54(1): 91-93.
Benowitz et al. "Metabolic and Psychophysiologic studies of cannabidiol hexobarbital interaction," Clin Pharmacol_Ther.., 28(1):115-120, 1980.
Bertram. "The Relevance od Kindling for Human Epilepsy," Apr. 1, 2007, 48(s2):65-74.
Bhatt et al. "Indigenous plants in traditional healcare system in Kedarnath valley of western HImalaya". Indian J Tradit Knowl. Apr. 2008;7(2):300-10.
Bhattacharyya et al. "Modulation of mediotemporal and ventrostriatal function in humans by Delta9-tetrahydrocannabinol: a nerual basis for the effects od Cannabis stava on learning and psychosis." Arch Gen Psychiatry. Apr. 2009;66( 4 ):442-51. doi: 10.1001/archgenpsychiatry.2009 .17.
Booth et al. "Legalization's opening of medical pot research is dream and nightmare," Denver Post, Dec. 14, 2013.
Bostanci et al. "The effects of octanol on penicillin induced epileptiform activity in rats: an in vivo study." Epilepsy Res. Oct. 2006;71(2-3): 188-94. Epub Jul. 27, 2006.
Bipolar Health Group (Charlotte's Web Hemp Remedy, available online at http://biopolarhealthgroup.org/index.php/charlottes-web-hemp-remedy/, accessed Sep. 6, 2017.
Braida et al. "Post-ischemic treatment with cannabidiol prevents electroencephalographic flattening, hyperlocomotion and neuronal injury in gerbils," Neuroscience Letters., 346:61-64, 2003.
Brust et al. "Marijuana use and risk of new onset seizures." Trans Am Clin Climatol Assoc. 1992; 103: 17 6-81.
Carlini et al. Hypnotic and antiepileptic effects of cannabidiol. J. Clin Pharmacol. Aug.-Sep. 1981;21(8-9 Suppl):417S-427S. Medline abstract only.
Cdc.gov [online], "2 to 20 yeras: Girls Stature-for-age and Weight-for-age percentiles," National Center for Health Statistics and National Center for Chronic Disease Prevention and Health Promotion, last modified Nov. 2000,<https://www.cdc.gov/growthcharts/data/set1clinical/cj4_11022.pdf>, 1 page.
Charlotte's Web [online], "When to Expect Results from CW Hemp Oil", Mar. 13, 2017, retrieved on May 21, 2018, URL https://www.cwhemp.com/blog/exvecting-results-from-hemp, 6 pages.
Charlotte's Web [online], "Whole-Plant Cannabinoids Outperform Single Molecule Compunds," CWHemp.com, Jan. 11, 2017, retrieved on Jun. 16,2 017, URL <https://www.cwhemp.com/blog/whole-plant-cw-hemp-cannabinoids>, 5 pages.
ChildNeurologyFoundation.org [online], "Disorder Directory: Learn from the Experts—LGS (Lennon-Gastaut Syndrome)," Child Neurology Foundation, available on or before Sep. 6, 2005, retrieved on May 21, 2018, URL http://www.childneurologyfoundation.org/disorders/lgslennox- gastaut-syndrome, 10 pages.
Chiron and Dulac. "The pharmacologic treatment of Dravet syndrome." Epilepsia. Apr. 2011; 52 Suppl 2:72-5. doi: 10.1111/j.1528-1167.2011.03007.x.
Castel-Branco et al. "The Maximal Electroshock Seizure (MES) Model in the Preclinical 98. Assessment of Potential New Anti epileptic Drugs," Methods Find Exp Clin Pharmacol., 31 (2); 101-106, 2009.
Chiu et al. "The Influence of Cannabidiol and the □9-Tetrahydrocannabinol on Cobalt Epilepsy in Rats," Epilepsia., 1979, 20:365-375.
Chou. "Theoretical basis, experimental design, and computerized simulation of synergism and antagonism in drug combination studies," Pharmacol Rev., Sep. 2006, 58(3), 621-681.
Combined Search and Examination Report in Application No. GB1611544.6, dated Mar. 29, 2017, 8 pages.
Conry et al. Epilepsia 2009, 50, 1158-1166 (Year: 2009).
Consroe et al. "Controlled clinical trial of cannabidiol in Huntington's Disease," Pharmacology Biochemistry & Behavior, 1991, 40:701-708.
Consroe et al. "Anticonvulsant nature of marihuana smoking." JAMA. Oct. 20, 1975;234(3):306-7.
Consroe et al. "Anticonvulsant drug antagonism of delta9tetrahydrocannabinol-insused seizures in rabbits." Res Commun Chem Pathol Pharmacol. Jan. 1977;16(1):1-13.
Consroe et al. "Anticonvulsant interaction of cannabidiol and ethosuximide in rats." J Pharm Pharmacol. Aug. 1977;29(8):500-1. doi: 10.1111/j.2042-7158.1977.tb11378.x.
Consroe et al. "Cannabidiol—antiepileptic drug comparisons and interactions in experimentally induced seizures in rats." J Pharmacol Exp Ther. Apr. 1977;201(1):26-32.
Consroe et al. "Effects of cannabidiol on behavioral seizures caused by convulsant drugs or current in mice." Eur J Pharmacol. Sep. 24, 1982;83(3-4):293-8.
Consroe et al. "Therapeutic Potential of Cannabinoids in Neurological Disorders," Chapter 2, pp. 21-49, Cannabinoids as Therapeutic Agents, R. Mechoulam, ed., CRC Press, Boca Raton (1986).
Consroe et al. Chapter 12, "Potential Role od Cmmabinoid for Therapy of Neurological Disorders," p. 459 in MariiuanaiCannabinoids: Neurobiology and Neurophvsiology, ed. L. Murphy (1992).
Crespel et al. "Lennox-Gastaut Syndrome," Chapter 14, in Epileptic Syndromes in Infancy, Childood, and Adolescence, 5th Edition, ed. M. Bureau et al. pp. 189-216.
Cortesi et al. "Potential therapeutical effects of cannabidiol in children wiht pharmacoresistant epilepsy." Med Hypotheses. 2007;68(4):920-1. Epub Nov. 16, 2006.

(56) References Cited

OTHER PUBLICATIONS

Cortez et al. Chapter 10 "Pharmacologic Models of Generalized Absence Seizures in Rodents," Models_Seizures Epilepsy ., 111-126, 2006.
Cunha et al. "Chronic administration of cannabidiol to healthy volunteers and epileptic patients." Pharmacology. 1980;21(3): 175-85.
Curia et al. "The pilocaipine model of temporal lobe epilepsy," J Neuroscience Methods, Jul. 2008, 172(2-4): 143-157.
Czapinski et al., "Randomized 36-month comparative study of valproic acid (VPA), phenytoin (PHT), phenobarbital (PB) and carbamazepine (CBZ) efficacy in patients with newly diagnosed epilepsy with partial complex seizures." J Neurolog Sci. Sep. 1997;150:S162.
Dasa et al. "Brhat Nighantu Ratnakara (Saligramanighantubhusanam)." vol. IV. 1997:170. Sanskrit. Exhibit 5.
Davis et al. "A predominant role for inhibition of the adenylate cyclase/protein kinase A pathway in ERK activation by cannabinoid receptor 1 in NIE-115 neuroblastoma cells." J Biol Chem. Dec. 5, 2003;278(49):48973-80. Epub Sep. 29, 2003.
Davis et al. "Antiepileptic action of marijuana-active substances." Federation Proceedings. 1949;8:284-5.
De Oliveira et al. "Anticonvulsant activity of β-caryophyllene against pentylenetetrazol-induced seizures." Epilepsy Behav. Mar. 2016;56:26-31. doi: 10.1016/j.yebeh.2015.12.040.
De Meijer. "Chapter 5: The Chemical Phenotypes (Chemotypes) of Cannabis," Handbook of Cannabis, ed. Roger G. Pertwee, 2014, 89-110.
Deshpande et al. Cannabinoid CB 1 receptor antagonists cause status epilepticus-like activity in the hippocampal neuronal culture model of acquired epilepsy. Neurosci Lett. Jan. 2007;41 1(1):1 1-6. Epub Nov. 15, 2006.
Devinsky et al. "Cannabidiol: Pharmacology and potential therapeutic role in epilepsy and other neuropsychiatric disorders," 2014 Epilepsia, 55(6), 791-802.
Dravet. The core Dravet syndrome phenotype. Epilepsia.52 Suppl 2:3-9. doi: 10.1111/j.1528-1167.2011.02994.x. (Year: 2011).
Dreifus et al. "Proposal for Revised Clinical and Electroencephalographic Classification of Epileptic Seizures," Epilepsie., 22:489-501, 1981.
Dulac. "Use of Lamotrigine in Lennox-Gastaut and Related Epilepsy Syndromes," J. Child Neurolog., 12(Supplement 1), S23-S29 (1997).
Dulac. "Vigabatrin in Childhood Epilepsy," J. Child Neurolog., 6(Supplement 2), S30-S37 (1991).
Eadie. "Shortcomings in the current treatment of epilepsy." Expert Rev Neurother. Dec. 2012;12(12):1419-27.
Engel. "Report of the ILAE classification core group." Epilepsia. Sep. 2006;47(9): 1558-68.
Engel et al. Chapter 1, "What Should be Modeled," In Models Seizure Epilepsy., 2006, 14 pages.
Eggers. "Temporal lobe epilepsy is a disease of faulty neuronal resonators rather than oscillators, and all seizures are provoked, usually by stress," Med Hypotheses.,69(6):1284-9, 2007.
Elsohly and Gul. "Constituents of Cannabis Sarvia," Chapter 1, Handbook of Cannabis, ed. Roger G. Pertwee, pp. 3-22 (2014).
EPO Third Party Observations in European Appln. No. EP10734514. 5, dated Apr. 3, 2017, 19 pages.
EPO Third Party Observations in European Appln. No. EP11712658. 1, dated Nov. 22, 2013, 14 pages.
FDA, "Warning Letters and Test Results for Cannabidiol-Related Products," 2016 Warning Letters.
FDA, "Warning LEtters and Test Results for Cannabidiol-Related Prodcuts," 2015 Warning Letters.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
Fariello. "Parenteral Penicillin in Rats: An Experimental Model of Multifocal Epilepsy," Epilepsia, 17:217-222, 1976.

Ferdinand et al. "Cannabis—psychosis pathway independent of other types of psychopathology." Schizophr Res. Nov. 15, 2005;79(2-3):289-95. Epub Aug. 25, 2005.
Fisher et al. The impact of epileps from the patient's perspective I. Descriptions and subjective perceptions. Epilepsy Res. Aug. 2000;41(1):39-51.
Gabor et al. Lorazepam versus phenobarbital : Candidates for drug of choice for treatment of status epilepticus. J Epilepsy. Jan. 1990;3(1):3-6.
Gallily et al. "Overcoming the Bell-Shaped Dose-Response of Cannabidiol by Using Cannabis Extract Enriched in Cannabidiol," Phannacolog_v_&_Pliarrnacv ., 6:75 1J85, Jan. 2015.
Gastaut. Clinical and electroencephalographical classification of epileptic seizures. Epilepsia. Mar. 1970;11(1):102-13.
Gardner [online], "Comes Now Epidiolex (FDA Approves IND Studies of CBD)," BeyondTHC.com, Oct. 22, 2013, retrieved on Jan. 31, 2018.
GB Combined Search and Examination Report in GB Appln. No. GB1116789.7, dated Jan. 4, 2012.
GB Combined Search and Examination Report in Application No. GB1611544.6, dated Mar. 29, 2017.
GB Combined Search and Examination Report in GB Appln. No. GB1100043.7, dated Mar. 25, 2011.
GB Combined Search and Examination Report in GB Appln. No. GB1121919.3, dated Feb. 29, 2012.
GB Combined Search and Examination Report in GB Appln. No. GB1410771.8, dated Feb. 27, 2015.
GB Combined Search and Examination Report in GB Appln. No. GB1414813.4, dated Sep. 5, 2014.
GB Combined Search and Examination Report in GB Appln. No. GB1418166.3, dated Jul. 2, 2015.
GB Combined Search and Examination Report in GB Appln. No. GB1418170.5, dated Jul. 2, 2015.
GB Combined Search and Examination Report in GB Appln. No. GB1418171.3, dated Jun. 29, 2015.
GB Combined Search and Examination Report in GB Appln. No. GB1506550.1 , dated Feb. 5, 2016.
GB Combined Search and Examination Report in GB Appln. No. GB1514079.1 , dated May 4, 2016, 9 pages.
GB Combined Search and Examination Report in GB Appln. No. GB1605448.8, dated Jan. 12, 2017, 6 pages.
GB Examination Report in GB Appln. No. GB1100043.7, dated Mar. 18, 2014, 2 pages.
GB Combined Search and Examination Report in GB Appln. No. GB1621480.1 , dated Sep. 22, 2017.
Gedde. "Clinical Experience with Cannabis in Treatment-Resistant Pediatric Epilepsy," http://www.theroc.us/images/gedde_presentation. pdf, Sep. 9-11, 2014.
Geffrey et al., "Cannabidiol (CBD) Treatment for Refractmy Epilepsy in Tuberous Sclerosis Complex (TSC)," American Epilepsv Socie1.v., Annual Meeting Abstacts: Vie•w, Abstract 2.427, 2014, retrieved on Feb. 10, 2017, 2 pages.
Green. "CBD: An Unconventional Therapy," available online at http://nugs.com/article/cbd-an-unconventional-therapv_.html, published Mar. 24, 2014, 5 pages.
Gresham et al "Treating Lennox-Gast.ant syndrome in epileptic pediatric patients with tlrirdgeneration mfinamide," Neurosvchiatr Dis Treat., 6:639-645, Oct. 5, 2010.
Gross et al. Marijuana use and epilepsy: prevalence in patients of a tertiary care epilepsy center. Neurology. Jun. 8, 2004;62(11 ):2095-7.
Grotenhermen. "Epilepsiebehandlung des Angelman-Syndroms mit CBD (Cannabidiol) (Epilepsy treatment of Angelman syndrome with CBD (cannabidiol)," Angelman e.V., Jan. 2015, retrieved on Jun. 7, 2019.
Guimaraes et al. "Antianxiety effect of cannabidiol in the elevated plus-maze," Psychopharmacology (Berl). 1990;100(4):558-9. doi: 10.1007/BF02244012.
Guerrini et al. "Lamotrigine and Seizure Aggravation in Severe Myoclonic Epilepsy," Epilepsia, 39(5):508-512, 1998.
GWPharm [online], "GW Pharmaceuticals Announces Epidiolex(R) Receives Fast Tract Designation from FD A for the Treatment of Dravet Syndrome," GW Pharmaceuticals Press Release, Jun. 6,

(56) References Cited

OTHER PUBLICATIONS 2014, retrieved on Mar. 1, 2017, URL <https://www.gwphann.com/about-us/news/gw-pharmaceuticals-announces-epidiolex%C2%AE-receives-fast-track-designation-fda-treatment>, 2 pages.

GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.

GWPharm [online], "GW Pharmaceuticals Provides Updated on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-pro_gram-childhood-epilepsy-epidiolex%C2%AE>, 5 pages.

GWPharm [online], "GW Pharmacuticals Recieves Orphan Drug Designation by FDA for Epidiolex® in the Treatment of Lennox-Gastuat Syndrome," GW Pharmaceuticals Press Release, Feb. 28, 2014, retrieved on Feb. 10, 2017, URL <https://www.gwphann.com/about-us/news/gw-pharmacuticals-receives-orphan-dmg-designation-fda-epidiolex%C2%AE-treatment-lennox>, 4 pages.

GWPharm [online], "Orphan Drug Designation Granted for Epidiolex in Dravet syndrome by the FDA—Seven Expended Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwphann.com/about-us/news/gw-pharmaceuticals-provides-update-orphan-program-childhood-epilepsy-epidiolex%C2%AE>, 5 pages.

GWPharm [online], "GW Pharmaceuticals Announces Preliminary Results of Phase 2a Study for its Pipeline Compund GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.

Heinemann et al. "An Overivew of in Vitro Seizure Models in Acute and Organtoypic Slices," Chapter 4, 35-44, 2006.

Hill et al. "Δ9-Tetrahydrocannabivarin suppresses in vitro epileptiform and in vivo seizure activity in adult rats." Epilepsia. Aug. 2010;51(8):1522-32. doi: 10.1111/j.1528-1167.2010.02523.x. Epub Feb. 26, 2010.

Hill. "Cannabidivarin-rich cannabis extracts are anticonvulsant in mouse and rat via a CB 1 receptor-independent mechanism," British Journal of Pharmacology, Oct. 2013, 170(3): 679-692.

Holmes et al. "Choosing the correct AED: From Animal Studies to the Clinic," Pediatr Neurol. Mar. 2008; 38(3): 151-162.

Iannotti et al. "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability." ACS Chem NeuroSci. Nov. 19, 2014;5(11):1131-41. doi: 10.1021/cn5000524.

ICE Epilepsy Alliance, The Dravet Syndrome Spectrum, Nov. 2008 (Year: 2008).

IUPHAR/BPS Guide to Pharmacology, Entry for Δ 9-tetrahydrocannabidiol available on or before Mar. 29, 2016.

Iuvone et al. "Neuroprotective effect of cannabidiol, a non-psychoactive component from Cannabis sativa, on beta-amyloid-induced toxicity in PC12 cells." J Neurochem. Apr. 2004;89(1 ): 134-41.

Izzo et al. "Non-psychotropic plant cannabinoids: new therapeutic opportunities from an ancient herb." Trends in Pharmacological Sciences. 30(10): 515-527, 2009.

Jacobson. "Survey of Cunent Cannabidiol Use in Pediatric Treatment-Resistant Epilepsy," Apr. 22, 2013.

Jeavons et al. "Sodium valproate in treatment of epilepsy." Br Med J. Jun. 15, 1974;2(5919):584-6.

Jones et al. [online], Info & Metrics / Article Information,"Cannabidiol Displays Antipileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/659/tab-article-info.

Joy et al. "Marijuana and Medicine. assessing the Science Base." National Academy Press. Washington D.C. 1999.

Kahan et al. "Rish of selection bias in randomized trials," Trials, 16: 405 (2015).

Karler et al. "The cannabinoids as potential antiepileptics." J Clin Pharmacol. Aug.-Sep. 1981;21(8-9 Suppl):437S-447S.

Karler et al. "The anticonvulsant activity of cannabidiol and cannabinol," Life Science,1973, 13: 1527-1531.

Kaplan. "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.

Kelley et al. "Doose syndrome (myoclonic-astatic epilepsy): 40 years of progress," Developemental Medicine & Child Neurology, Aug. 2010, 52: 988-993.

Kansas City Star, Missouri House passes cannabis extract legislation, Apr. 24, 2014.

Khan et al. Muheet-e-Azam, vol. II. 1887: 147. Persian. Exhibit 1.
Khan et al. Khazaain-al-Adiva. vol. I. 1911:885. Urdu. Exhibit 7.
Khan et al. Khazaain-al-Adiva. vol. I. 1911:886. Urdu. Exhibit 4.
Khan et al. Khazaain-al-Advia, vol. I. 1911: 889. Urdu. Exhibit 3.
Khan et al. Khazaain-al-Advia, vol. I. 1911: 889. Urdu. Exhibit 4.

Klitgaard et al. "Eletrophysiological, neurochemical and regional effects of levitracetam in the rat pilocarpine model of temporal lobe epilepsv," Seizure., 12(2):92-100, Mar. 2003.

Klitgaard et al. "Evidence for unique profile of levetiracetam in rodent models of seizures and epilepsy." European journal of pharmacology. Jul. 24, 1998, 353(2): 191-206.

Kramer et al. "Febrile infection-related epilepsy syndrome (FIRES): pathogenesis, treatment, and outcome: a multicenter study on 77 children." Epilepsia. Nov. 2011;52(11): 1956-65.

Kruk-Slomka et al. "A comparison of mecamylamine and bupropion effects on memory-related responses induced by nicotine and scopolamine in the novel okect recognition test in mice," Pharmacological Reports, Awmst 2014, 66(4): 638-646.

Kurz and Blass. "Use of dronabinol (delta-9-THC) in autism: a prospective single-case-study with an early infantile autistic child," Cannabinoids, 5(4): 4-6.

Kuhn et al. "Potent activity of carfilzomib, a novel, irreversible inhibitor of the ubiquitin-proteasome pathway, against preclinical models of multiple myeloma," Blood, Nov. 2007,110(9):3281-3290.

Kwan et al. Definition of drug resistant epilepsy: consensus proposal by the ad hoc Task Force of the ILAE Commission on Therapeutic Stategies, Epilepsia. Jun. 2010;51(6):1069-77.

Laprairie et al. "Cannabidiol is a negative allosteric modulator of the cannabidinoid CB 1 receptor," British J Pharmacology, 2015, 172(20): 4790-4805.

LeafScience.com [online], "What are the Highest CBD Strains!" Oct. 15, 2014, retrieved on Feb. 16, 2017, URL www.leafscience.com/2014/10/15/highest-cbd-strains/.

Leo et al. "Cannabidiol and epilepsy: Rationale and therapeutic potential," Pharmacological Research, Mar. 2016, 107: 85-92.

Lewis. "Mystery Mechanisms," The Scientist.com, Jul. 29, 2016, retrieved on Nov. 8, 2017, 2 pages.

Lieu et al. "Assessment of self-selection bias in a pediatric unilateral heraing loss study," Otolarvnzol Head Neck Surz. 142(3): 427-433 (2010).

Lindamood and Colasanti. Effects of delta 9-tetrahydrocannabionol and cannabidiol on sodium-dependent high affinity choline uptake in the rat hippocampus. J Pharmacology Experimental Therapeutics, 1980, 213(2):216-221.

Long et al. The pharmacological actions of cannabidiol. Drugs of the Future. Jul. 2005;30(7):747-53.

Loscher and Schmidt. "Modern antiepileptic drug development has failed to deliver: ways out of the current dilemma." Epilepsia. Apr. 2011;52(4):657-78. doi: 10.1111/j.1528-1167.2011.03024.x.

(56) References Cited

OTHER PUBLICATIONS

Lutz. "On-demand activation of the endocannabinoid system in the control of neuronal excitability and epileptiform seizures." Biochem Pharmacol. Nov, 1, 2004;68(9):1691-8.
Lowenstein. "Chapter 363: Seizures and Epilepsy," Diseases of the Central Nervous System, 2008, 2498-2512.
Luttjohann et al. "A revised Racine's scale for PTZ-induced seizures in rats." Physiol Behav. Dec. 7, 2009;98(5):579-86. doi: 10.1016/j.physbeh. 2009.09.005.
Maa et al. The case for medical marijuana in epilepsy. Epilepsia. Jun. 2014;55(6):783-6. doi: 10.1111/epi.12610.
Mackie. Cannabinoid receptors as therapeutics targets. Annu Rev Pharmacol Toxicol. 2006;46: 101-22.
Majoosi et al. Kaamil-al-Sena'ah, Part II, Central Council for Research in Unani Medicine. 2005: 116. Arabic. Exhibit 2.
Mattson et al. "Comparison of carbamazepine, phenobarbital, phenytoin, and piimidone in partial and secondarily generalized tonic-clonic seizures," N. Engl. J. Med, 313(3): 145-151, Jul. 18, 1985.
Mattson et al. "Prognosis for total control of complex partial and secondary generalized tonic clonic seizures," Neurology . . . 47:68-76, 1996.
Mares et al. "Electrical Stimulation-Induced Models of Seizures in Model of Seizures and Epilepsy Asla Pitkanen," Philip A. Schwartzkroin & Solomon L. Mose, eds.), 2004.
Martin et al. "Stmcture-Anticonvulsant Activity Relationships of Cannabidiol Analogs," National Insitute on Drug Abuse, Research Monograph Series, 1987, 79:48-58.
McNamara. "Chapter 19: Pharmacotherapy of the Epilepsies,", Goodman & Gilman's The Pharmacological Basis of Therapeutics 11th ed., McGraw-Hill Companies, 2006, 501-525.
Miller et al. "Mapping genetic modifiers of survival in a mouse model of Dravet syndrome," Genes, Brain and Behavior (2014) 13: 163-172.
Merlis, Proposal for an international classifciation of the epilepsies. Epilepsia. 1970.
Morard et al. "Conversion to Sirolimus-Based Immunosuppression in Maitenance Liver Transplantation Patients," Liver Transplantation, 13:658-664, 2007.
Malfait et al. "The nonpsychoactive cannabis constituent cannabidiol is an oral anti-arthritic therapeutic in murine collagen-induced arthritis," PNAS, Aug. 15, 2000, 97(17):9561-9566.
Manno. "Status Epilepticus: Current Treatment Strategies," The Neurohospitalist. Jan. 2011, 1(1):23-31.
Mechoulam et al. Toward drugs derived from cannabis. Naturwissenschaften. Apr. 197;65(4): 174-9.
Mechoulam et al. "Cannabidiol: An Overview of Some Pharmacological Aspects," J Clin Pharmacol. 2002, 42:11S-19S.
Morelli et al. "The effects of cannabidiol and its synergism with bortezomib in multiple myeloma cell lines. A role for transient receptor potential Vanilloid type-2," Int J Cancer, Jun. 2014, 134(11): 2534-2546.
MyVirtualMedicalCentre [online], "Aicardi syndrome," mvmc.com, Feb. 2004.
Nabissi et al. "Cannabinoids synergize with cafilzomib, reducing multiple myeloma cells viabity and migration," Oncotarget, Oct. 2016, 7: 77553.
Ng et al. Illicit drug use and the risk of new-onset seizures. Am J Epidemiol. Jul. 1990; 132(1):47-57.
Neto et al. "The role of polar phytocomplexes on anticonvulsant effects of leaf extracts of Lippia Alba (Mill.) N.E. Brown chemotypes," J. Pharm Pharmacol. 61(7):933-9 (2009).
Obay et al. Antiepileptic effects of ghrelin on pentylenetetrazole-induced seizures in rats. Peptides. Jun. 2007;28(6): 1214-9. Epub Apr. 19, 2007.
Oakley et al. "Dravey Syndrome Insights into pathophysiology and therapy from a mouse model of Dravet syndrome," Epilepsia 52(Suppl. 2):59-61 (2011).
PCT International Preliminary Report on Patentability in International Appl. No. PCT/GB2017/052229, dated Feb. 26, 2019.

PCT International Preliminary Report on Patentability in International Appl. No. PCT/GB2017/053735, dated Mar. 14, 2018.
PCT International Preliminary Report on Patentability in International Appl. No. PCT/GB2017/052229, dated Oct. 6, 2017.
PCT International Preliminary Report on Patentability in International Appl. No. PCT/GB2010/051066, dated Jun. 9, 2011.
PCT International Preliminary Report on Patentability in International Appl. No. PCT/GB2012/052284, dated Dec. 12, 2013.
PCT International Preliminary Report on Patentability in International Appl. No. PCT/GB2015/051775, dated Aug. 10, 2016.
PCT International Preliminary Report on Patentability in International Appl. No. PCT/GB2015/053030, dated Apr. 18, 2017.
PCT International Preliminary Report on Patentability in International Appl. No. PCT/GB2016/051792, dated Sep. 1, 2017.
PCT International Search Report and Written Opinion in International Appl. No. PCT/GB2010/051066 dated Dec. 13, 2010.
PCT International Search Report and Written Opinion in International Appl. No. PCT/GB2011/050649, dated May 30, 2011.
PCT International Search Report and Written Opinion in International Appl. No. PCT/GB2012/052284, dated Nov. 16, 2012.
PCT International Search Report and Written Opinion in International Appl. No. PCT/GB2015/051775, dated Aug. 26, 2015.
PCT International Search Report and Written Opinion in International Appl. No. PCT/GB2015/051776, dated Aug. 25, 2015.
PCT International Search Report and Written Opinion in International Appl. No. PCT/GB2017 /051943, dated Sep. 12, 2017.
PCT International Search Report and Written Opinion in International Appl. No. PCT/GB2016/052340, dated Oct. 25, 2016.
PCT International Search Report in International Appln. No. PCT/GB2012/050002, dated Feb. 24, 2012.
PCT International Preliminary Report on Patentability in International Appln. No. PCT/US2017/050868, dated Oct. 11, 2018.
PCT International Search Report and Written Opinion in International Appln. No. PCT/US2017/050868, dated Aug. 6, 2017.
PCT International Search Report and Written Opinion in International Appln. No. PCT/GB2017/051913, dated Sep. 15, 2017.
PCT International Search Report and Written Opinion in International Appln. No. PCT/GB2017/051914, dated Sep. 12, 2017.
Physician's Desk Reference, 63rd Ed., 2009, 423-431, 2192-2194, 2639-2242, 3019-3022.
Pelliccia et al. "Treatment with CBD in oily solution of drug-resistant paediatric epilpesies," Availabe online Sep. 2, 2010, Retrieved Jun. 30, 2015, retrieved from the interenet.
Pereira et al. Study pharamacologic of the GABAergic and glutamaterigic drugs on seizures and status epilepticus induced by pilocarpine in adult Wistar rats. Neurosci Lett. Jun. 4, 2007;419(3):253-7. Epub Apr. 13, 2007.
Pertwee. Cannabinoid receptor ligands: clinical and neuropharmacological considerations, relevant to futre drug discovery and development. Expert Opin Investig Drugs. Jul. 2000;9(7): 1553-71.
Pertwee. "The diverse CB1 and CB2 receptors pharmacology of three plant cannabinoids: Alpha9 Tetrahydrocannabinol, cannabidol, and alpha9-tetrahydrocannabivarin," BR. J. Pjharmacol. 153 (2): 199-215, 2008.
Pertwee. "Chapter 3: The Pharmacology and Therapeutic Potential of Cannabidiol," Cannabinoids, Ed Vincenzo Di Marzo ed., 2004, 32-83.
Petrocellis, et al., "Effects of cannabinoids and cannabinoid-enriched Cannabis extracts on TRP channels and endocannabinoid metabolic enzymes," British Journal of Pharmacology (2011) 163 1479-1494.
Pohl et al. Effects of flunarizine on Metrazol-induced seizures in developing rats. Epilepsy Res. Sep. 1987;1(5):302-5.
Poortman-Van Der Meer. "A contribution to the improvement of accuracy in quantitation of THC," Forensic Science International, Apr. 1999, 101(1): 1-8.
Pouton. "Lipid formulations for oral administration of drugs: non-emulsifying, self-emulsifying and 'self-microemulsifying' drug delivery systems," Eur. J Phann Sci, Oct. 2000, 11(Supp. 2): S93-S98.
Press et al. Parental reporting of response to oral cannabis extracts for treatment of refractory epilepsy. Epilepsy Behav. Apr. 2015;45:49-52. doi: 10.1016/j.yebeh.2015.02.043. Epub Apr. 3, 2015.

(56) References Cited

OTHER PUBLICATIONS

Pruitt et al. "Ethanol in Liquid Preparations Intended for Children," Padiatrics, Mar. 1984: 73(3): 405-407.

Raab et al. "Multiple myeloma," Lancet, Jul. 2009, 374(9686): 324-339.

Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.

Ramantani et al., "Epilepsy in Aicardi—Goutieres syndrome," Official J Eur Paediatric Neurology Society, 2014, 18: 30-37.

Rauca et al. The role of superoxide dismutase and alpha-tocopherol in the development of seizures and kindling induced by pentylenetetrazol—influence on the radical scavenger alpha-phenyl-N-tert-butyl nitrone. Brain Res. May 29, 2004;1009(1-2):203-12.

Resstel et al. 5-HTIA receptors are invovled in the cannabidiol-induced attenuation of behavioural and cardiovascular responses to acute restraint stress in rats. Br J Pharmacol. Jan. 2009;156(1): 181-8.

Rosenberg et al. "Cannabinoids and Epilepsy," Neurotherapeutics, Oct. 2015, 12(4): 747-768.

Rosenkrantz, et al., "Oral and Parenteral Formulations of Marijuana Constituents," J Pharm Sci, Jul. 1972,61(7)1106-1112.

Russo. Taming THC: potential cannabis synergy and phytocannabinoid-termoid entourage effects 163 British J. of Pharm. 1333 (2011).

Rubio et al. "In vivo Experimental Models of Epilepsy," Central Nervous System Agents in Medicinal Chemistry, 10:298-309, 2010.

Sadanandasarma et al. Rasatarangini. 11th Ed. 1979:720-3. Sanskrit. Exhibit 6.

Sander. The epidemiology of epilepsy revisited. Curr Opin Neural. Apr. 2003; 16(2): 165-70.

Sandy et al. "Preliminary trial of cannabidiol in Huntongton's Disease," Marihuana: An International Research Report, 1988, 157-162.

Sastri et al. Anandakandam. 1st Edition. 1952:241. Sanskrit. Exhibit 2.

Scuderi et al Cannabidiol in medicine: a review of its therapeutic potential in CNS disorders. Phytoher Res. May 2009;23(5):597-602.

Silva et al. Can J. Neurol. Sci. 2006 vol. 33 pp. 783-786.

Shukla [online], "New Automated Purification Strategies for Scale-Up," PCISyntesis.com, posted Dec. 25, 2017, https://www.pcisynthesis.com/new-automated-purification-strategies-for-scaleup/,5 pages.

Sperling et al. "Carisbamate as adjunctive treatment of partial onset seizures in adults in two randomized, placebo-controlled trials," Epilepisa Mar. 2010;51(3):333-43.

Swann et al. The effects of seizures on the connectivity and circuitry of the developing brain. Ment Retard Dev Disabil Res Rev. 2004; 10(2):96-100.

Stafstrom et al. "Models of Pediatric Epilepsies: Stategies and Opportunities," Epilepsia, vol. 47, No. 8, 2006.

Stephenson. "In Memoriam: Professor Jean Aicardi (1926-2015)," Pediatric Neurology, Jan. 2016, 54: 3-4.

Strickley. "Solubilizing Excipients in Oral and Injectable Formulations," Table VIII, Pharmaceutical Research, Feb. 2004, 21(2): 201-230.

Stott et al. Cannabinoids for the pharmaceutical industry. Euphytica. 2004;140:83-93.

Thomas et al., Evidence that the plant cannabinoid Delta9-tetrahydrocannabivarin is a cannabinoid CBI and CB2 receeopter antagonist. Br J Pharmacol. Dec. 2005;146(7):917-26.

Thomas et al. "Cannabidiol displays unexpectedly high potency as an antagonist of CB 1 and CB2 receptor agonists in vitro," British J Pharmacology, 2007, 150(5): 613-623.

Thurman et al., Standards for epidemiologic studies and surveillance of epilepsy. Epilepsia. Sep. 2011;52 Suppl 7:2-26. doi:10.1111/j.1528-1167.2011.03121.x.

Thumma et al. "Influence of plasticizers on the stability and release of a prodmg of ./19-tetrahydrocannabinol incoiporated in poly (ethylene oxide) matrices," Eur J Pharmceutics and Biopharmaceutics, Oct. 2008, 70(2): 605-614.

Thurstone (Avoid Charlotte's Web for Epilepsy, available online at http://drthurstone.com/charlotted-web-not-safest-option-epilepsy-treatment/, published Jun. 26, 2014.

Trembly et al., Double-blind clinical study of cannabidiol as a secondary anticonvulsant. Marijuana '90 International Conference on Cannabis and Cannabinoids. Kolymbari, Crete. Jul. 8-11, 1990.

Turkanis et al. "An Electrophysiological Analysis of the Anticonvulsant Action of Cannabidiol on Limbic Seizures in Conscious Rats," Epilepsia., 20:351-363, 1979.

Usami et al. Synthesis and pharmacological evaluation in mice of halogenated cannabidiol derivatives. Chem Pharm Bull (Tokyo). Nov. 1999;47(11):1641-5.

Unimed Pharmaceuticals, Inc., "Marinol®," Jul. 2006 <https://www.accessdata.fda.gov/dmgsatfda_docs/label/2006/018651s025s0261b1.pdf>, 11 pages.

USPTO Decision on Appeal in U.S. Appl. No. 10/318,659 (Appeal 2009-011751), dated Jul. 8, 2010.

USPTO Decision on Appeal in U.S. Appl. No. 13/698,730 (Appeal 2016-006358), dated Jun. 21, 2017.

USPTO Information Disclosure Statement Form PT0-1449 in U.S. Appl. No. 13/380,305, dated Nov. 24, 2014.

USPTO Notice of Allowance in U.S. Appl. No. 13/380,305, dated Dec. 10, 2014.

USPTO Notice of Allowance in U.S. Appl. No. 13/380,305, dated Mar. 19, 2015.

USPTO Office Action in U.S. Appl. No. 13/380,305, dated Aug. 25, 2014.

USPTO Request for Continued Examination with the Amendment and Information Disclosure Statement in U.S. Appl. No. 13/380,305, filed Mar. 2, 2015.

USPTO Third Preliminary Amendment under 37 C.F.R. 1.115 in U.S. Appl. No. 13/380,305, dated May 23, 2014, 4 pages.

Utah.gov [online], "2nd Agenda Controlled Substances Advisory Committee Meeting," Nov. 12, 2013, URL <httos://www.utah.gov/pmn/files/81459.pdt>.

Van Rijckevorsel. Neuropsychiatr Dis Treat. Dec. 2008; 4(6): 1001-1019.

Velasco et al. "Anticancer mechanisms of cannabinoids," Curr Oncol, Mar. 2016, 23(2): S23-S32.

Velisek. "Models of Chemically-Induced Acute Seizures," Models Seizure Epilepsy, 127-152, 2006.

Veliskova. Chapter 48 "Behavioral Characterization of Seizures in Rates," Model Seizures Epilepsy, 601-611, 2006.

Vollner et al. Haschisch XX: Cannabidivarin, ein neuer Haschisch-Inhaltsstoff. Tetrahedron Lett. 1969;10(3):145-7.

Wahle et al. Development of tolerance to the anticonvulsant effect of valproate but not to ethosuximide in a rat model of absence epilepsy. Eur J Pharma. May 1990;181(1-2):1-8.

Wallace et al. "Pharmacoptherapy for Dravet Syndrome," Pediatr. Drugs, 18:197-208 (2016).

Wallace et al. Assessment of the role of CB 1 receptors in cannabinoid anticonvulsant effects. Eur J Pharmacol. Sep. 28, 2001;428(1):51-7.

Weston et al. Tetrahydrocannabivarin exhibits anticonvulsant effects in a piriform cortical brain slice model of epileptiform activity. Pro British Pharm Soc 75th Anniv Meeting. Dec. 31, 2006. Found on: http://www.pA2online.org/abstract/abstract.jsp?abid=28533. Abstract Only. 1 page.

Wingerchuk. Cannabis for medical purposes: cultivating science, weeding out the fiction. Lacet. Jul. 24-30, 2004;364(9431):315-6.

Wikipedia.org [online], "Cannabinoid," Wikipedia, Apr. 2003, retrieved on Mar. 1, 2017, URL<https://en.wikipedia.org/wiki/Cannabinoid>, 15 pages.

Yu et al. "Reduced sodium current in GABAergic intemeurons in a mouse model of severe myoclonic epilepsy in infancy," Nature Neurosience vol. 9, No. 9, Sep. 2006, pp. 1142-1149.

Yuriev. Endogenic cannabinoid system is a new perspective object of pharmacotherapeutic effect to disease of nervous system, Ukrainsky Metodichny Chasopis, 2005; 6(50): 21-9.

(56) References Cited

OTHER PUBLICATIONS

Zamberletti et al. "Alternations of prefrontal cortex GABAergic transmission in the complex 26. psychotic-like phenotype induced by adolescent delta-9-tetrahydrocannabinol exposure in rats," Neurobiology of Disease, Mar. 2014, 63: 35-47.

Zhao et al. Chapter 27 "Repetitive Seizures in the Immature Brain," Models Seizures Epilsepsy, 341-350, 2006.

Zhornitsky and Potvin. "Cannabidiol in Humans—The Quest for Therapeutic Targets," Pharmaceuticals, 2012, 5:529-552.

Zuardi et al. Cannabidiol, a Cannabis sativa constituent, as an antipsychotic drug. Braz J Med Biol Res. Apr. 2006;39(4):421-9. Epub Apr. 3, 2006.

Zuardi et al. "Cannabidiol: from an inactive cannabinoid to a drug with wide spectrum of action," Rev Bras Psiquiatr, 2008, 30(3): 271-80.

[Anonymous], High Times [online]; 2017, downloaded from: https://hightimes.com/edibles/2017-socal-canabis-cup-top-10-edibles/ on Dec. 15, 2022, 3 pages.

[Anonymous], Potvalet [online]; 2017; downloaded from https://www.pitvalet.com/products/cbd-thc-gel-caps-1-1/ on Dec. 15, 2022, 2 pages.

Crodesta F10 [online] retrieved on Feb. 4, 2023 from: https://www.ulprospector.com/en/na/PersonalCare/Detail/134/30883/Crodesta-F10; 2 pages. (Year: 2023).

Li, C. L. et al., "The use of hypromellose in oral drug delivery," Journal of Pharmacy and Pharmacology, 57:533-546 (2005).

\* cited by examiner

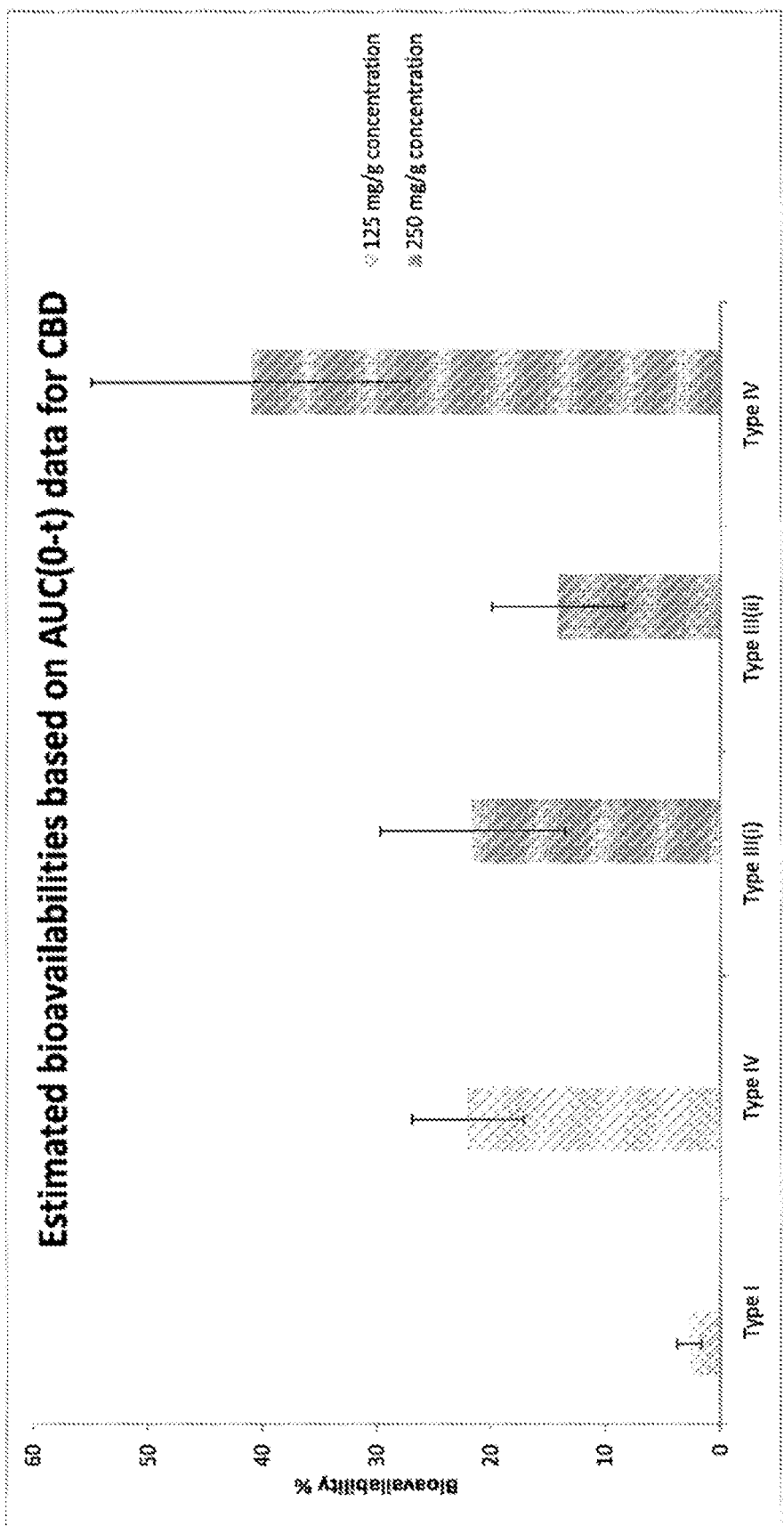

PHARMACEUTICAL COMPOSITION COMPRISING A CANNABINOID

CROSS-REFERENCE TO RELATED APPLICATIONS

This application claims the benefit of International PCT Application No. PCT/GB2019/050007, filed Jan. 2, 2019; and Great Britain Application No. 1800072.9, filed Jan. 3, 2018; all of which are incorporated herein by reference in their entirety.

FIELD OF THE INVENTION

The present invention relates to an oral pharmaceutical formulation contained in a container. The oral pharmaceutical formulation comprises a cannabinoid.

BACKGROUND OF THE INVENTION

Cannabinoids are lipophilic substances that are known to be poorly soluble in water (less than 1 μg/mL). As an example, cannabidiol (CBD) is soluble in ethanol (36 mg/mL) and dimethylsulfoxide DMSO (60 mg/mL).

Bioavailability of pharmaceutical substances taken perorally, first of all, depends on the extent to which the pharmaceutically active substance is absorbed from the intestinal environment across the intestinal mucosa. Lipophilic pharmaceutical substances are generally poorly absorbed from the intestinal environment, inter alia because of their poor solubility and/or dispersibility in water. Bioavailability of a pharmaceutical substance taken perorally furthermore depends on the susceptibility of the substance to the so-called first pass effect. Substances absorbed from the intestine, before being distributed throughout the body, have to pass the liver first where they may be metabolised immediately. CBD is generally assumed to be rather susceptible to first-pass liver metabolisation. Oral bioavailability of CBD is low and unpredictable (S. Zhornitsky, S. Potvin, Pharmaceuticals (2012) 5, 529-552). In addition, CBD is an unstable drug (A. J. Poortman, H. Huizer, Forensic Science International (1999) 101, 1-8).

In WO 2012/033478, Self-Emulsifying Drug Delivery Systems (SEDDS) have been used to offer improved administration of cannabinoids.

SEDDS (self-emulsifying drug delivery systems) generally consist of hard or soft capsules filled with a liquid or a gel that consists of lipophilic active pharmaceutical ingredient (API), oil (to dissolve the API) and a surfactant. Upon contact with gastric fluid, the SEDDS spontaneously emulsify due to the presence of surfactants. Many surfactants, however, are lipid based and interact with lipases in the gastro intestinal tract (GIT). This can lead to a reduced capability of the lipid based surfactants to emulsify the API as well as the oil carrier, both reducing bioavailability.

In WO 2015/184127, an alcohol-free formulation comprising a cannabinoid, a polyethylene glycol and propylene glycol is disclosed.

In WO 2012/033478, SEDDS formulations based on Type I, Type II and Type III were utilised.

In PCT/GB2017/051943 (as yet unpublished) a Type IV or Type IV-like formulation comprising a cannabinoid is disclosed.

Other documents relevant to the background of the present invention are CN103110582, CN101040855, US2012/183606; Thumma S Et Al, European Journal of Pharmaceutics and Biopharmaceutics. vol 70, no. 2, 1 Oct. 2008, pp 605-614; and Edward Maa Et Al, Epilepsia, vol. 55, no. 6, 1 Jun. 2014, pp 783-786.

The Lipid Formulation Classification System (LFCS) was introduced to help identify the characteristics of lipid systems (C. W. Pouton, Eur. J. Pharm. Sci., 11 (Suppl. 2) (2000), pp. S93-S98). As classified in the LFCS, Type I formulations are oils which require digestion, Type II formulations are water-insoluble self-emulsifying drug delivery systems (SEDDS), Type III systems are SEDDS or self-micro emulsifying drug delivery systems (SMEDDS) or self-nano emulsifying drug delivery systems (SNEDDS) which contain some water-soluble surfactants and/or co-solvents (Type IIIA) or a greater proportion of water soluble components (Type IIIB). Category Type IV represents a recent trend towards formulations which contain predominantly hydrophilic excipient surfactants and co-solvents. Below is a tabular Lipid Formulation Classification System overview taken from US 2015/111939:

| Excipients in formulation | Content of formulation (wt.-%) | | | | |
|---|---|---|---|---|---|
| | Type I | Type II | Type IIIA | Type IIIB | Type IV |
| Oil: triglycerides or mixed mono- and diglycerides | 100 | 40-80 | 40-80 | <20 | — |
| Water-insoluble surfactants (HLB < 12) | — | 20-60 | — | — | 0-20 |
| Water-soluble surfactants (HLB > 12) | — | — | 20-40 | 20-50 | 30-80 |
| Hydrophilic co-solvent | — | — | 0-40 | 20-50 | 0-50 |

A further description of the Lipid Formulation Classification System can also be found in FABAD J. Pharm. Sci., pages 55-64, 2013.

As can be seen in the above table, Type IIIB formulations comprise <20 wt % of oil, based on the total composition. However, it should be noted that, by definition, Type IIIB formulations contain some oil, even if it is only a very small amount.

Exposure of pharmaceutical substances that are sensitive to moisture, oxygen and/or light can lead to serious consequences. For example, exposure may cause softening and disaggregation of the product, and can degrade the active ingredients, for example by hydrolysis, photolysis and oxidation. Ultimately if a drug proves unstable it may not pass clinical trials. Damage to a pharmaceutical product exposed to the environment may be quantified by measuring the amount of degradants of the pharmaceutical product ingredients, e.g. active ingredient, as well as the amount of ingredients per se. Furthermore, aliquots may be taken and analysed at specified periods to obtain a profile of the stability of a pharmaceutical product stored under certain conditions.

Cannabinoids are susceptible to degradation through exposure to the environment, for example through exposure to light, heat, oxygen and/or moisture.

The cannabinoid tetrahydrocannabinol (THC) is degraded on exposure to environmental factors to the cannabinoid cannabinol (CBN). This cannabinoid binds to different receptors and has a different physiological effect on the human body and as such degradation of cannabinoids is detrimental when they are to be used as pharmaceutical active ingredients.

There exists a need to provide protection of pharmaceutical formulations comprising cannabinoids to maintain the physical and chemical stability of the pharmaceutical product.

There exists a need to provide an oral pharmaceutical formulation comprising a cannabinoid that exhibits improved properties such as bioavailability, storage stability and homogeneity.

BRIEF SUMMARY OF THE INVENTION

The present invention relates to a novel cannabinoid oral pharmaceutical dosage form, based on a Type IV or Type IV-like formulation, as classified using the Lipid Formulation Classification System. The formulation is contained in a container. By Type IV-like, it is meant that the formulation comprises no oil, for example no triglycerides or mixed glycerides. When a Type IV-like formulation is used, it may comprise more than the 50 wt % of solvent, based on the total composition, as specified in the LFCS table.

The oral pharmaceutical dosage form or formulation comprises at least one cannabinoid; at least one poloxamer; and a solvent, wherein the solvent is defined according to formula (I)

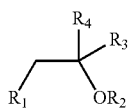
(I)

wherein $R_1$ and $R_2$ are independently selected from hydrogen, $C(O)CH_3$, OH, $C(O)CH_3$, $CH_2OH$ and $C(O)OCH_2CH_3$; $R_3$ is independently selected from $CH_3$, $CH_2OH$, OH, $CH_2OC(O)CH_3$ and $CH_2C(O)CH_2CH_3$; and $R_4$ is independently selected from hydrogen and $C(O)OCH_2CH_3$. The oral pharmaceutical formulation is contained in a container.

The invention also relates to an oral pharmaceutical unit dosage form comprising a pharmaceutical formulation, said pharmaceutical formulation comprising at least one cannabinoid; at least one poloxamer; and a solvent, wherein the solvent is defined according to formula (I)

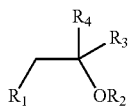
(I)

wherein $R_1$ and $R_2$ are independently selected from hydrogen, $C(O)CH_3$, OH, $C(O)CH_3$, $CH_2OH$ and $C(O)OCH_2CH_3$, $R_3$ is independently selected from $CH_3$, $CH_2OH$, OH, $CH_2OC(O)CH_3$ and $CH_2C(O)CH_2CH_3$, and $R_4$ is independently selected from hydrogen and $C(O)OCH_2CH_3$. The unit dosage form is contained in a container.

The invention also relates to a pharmaceutical package, wherein the pharmaceutical package contains an oral pharmaceutical formulation (or at least one unit dosage form comprising the oral pharmaceutical formulation), the oral pharmaceutical formulation comprising at least one cannabinoid; at least one poloxamer; and a solvent, wherein the solvent is defined according to formula (I)

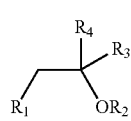
(I)

wherein $R_1$ and $R_2$ are independently selected from hydrogen, $C(O)CH_3$, OH, $C(O)CH_3$, $CH_2OH$ and $C(O)OCH_2CH_3$, $R_3$ is independently selected from $CH_3$, $CH_2OH$, OH, $CH_2OC(O)CH_3$ and $CH_2C(O)CH_2CH_3$, and $R_4$ is independently selected from hydrogen and $C(O)OCH_2CH_3$.

This formulation enhances cannabinoid bioavailability compared to other formulations based on Type I, Type II, Type IIIA and Type IIIB, as classified by the Lipid Formulation Classification System. Accordingly, the oral pharmaceutical dosage form or formulation is not oil-based, i.e. it comprises substantially no oil. By "substantially no oil" or "substantially oil-free", it is meant that the formulation comprises less than 2 wt % oil, preferably less than 1 wt % based on the total composition. Such formulations are classified as Type IV or Type IV-like.

By enhancing bioavailability, the total amount of cannabinoid and excipients required during a certain window of time in a treatment of a specific disease may be reduced.

The formulation according to the present invention exhibits excellent stability under various, in particular dry, storage conditions.

By enhancing stability, the length of time for which the formulations are fit for consumption, in particular oral administration, may be increased.

BRIEF DESCRIPTION OF THE DRAWING

The FIGURE shows estimated bioavailabilities (%) for Type I, Type III and Type IV formulations having CBD concentrations of 125 mg/g and 250 mg/g.

DETAILED DESCRIPTION OF THE INVENTION

The Cannabinoid

The formulation according to the present invention comprises at least one cannabinoid selected from the group consisting of cannabichromene (CBC), cannabichromenic acid (CBCV), cannabidiol (CBD), cannabidiolic acid (CBDA), cannabidivarin (CBDV), cannabidivarinic acid (CBDVA), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA). This list is not exhaustive and merely details the cannabinoids which are identified in the present application for reference. So far, over 100 different cannabinoids have been identified and these cannabinoids can be split into different groups as follows: Phytocannabinoids; Endocannabinoids; and Syntho-cannabinoids. Preferably the cannabinoid used in the present invention is at least one selected from the group consisting of phytocannabinoids and endocannabinoids. The phytocannabinoids and endocannabinoids may be synthetically produced or highly purified from their natural source.

The formulation according to the present invention may also comprise at least one cannabinoid selected from those disclosed in Handbook of Cannabis, Roger Pertwee, Chapter 1, pages 3 to 15.

It is preferred that the formulation comprises only one or two cannabinoids, which are preferably selected from the group consisting of, cannabidiol (CBD), cannabidivarin (CBDV), tetrahydrocannabinol (THC), tetrahydrocannabivarin (THCV), cannabigerol (CBG) and cannabidiolic acid (CBDA) or a combination thereof. It is preferred that the formulation comprises cannabidiol and/or cannabidivarin.

It is preferred that the formulation comprises tetrahydrocannabinol (THC) (or analogues thereof, such as THCV, THCA and THCVA) and cannabidiol (CBD) (or analogues thereof, such as CBDV, CBDA and CBDVA).

It is preferred that the cannabinoid is present in an amount of from about 5 to 80 wt %, based on the total composition, preferably from about 10 to 50 wt %, more preferably from about 20 to 30 wt %. The cannabinoid may be present in an amount of about 30 wt %.

Preferably, the cannabinoid is synthetically produced or highly purified from its natural source (for example, plant derived recrystallized form, such as a plant derived recrystallized form of CBD). When a highly purified source is used, it is purified such that the cannabinoid is present at greater than 95%, more preferably greater than 98% of the total extract (w/w). Use of a synthetically produced or highly purified cannabinoid is advantageous because these contain relatively low amounts of wax. This assists in prevention of the formation of an oily formulation, increasing physical stability of the formulation and wettability in an aqueous environment.

When the formulation comprises tetrahydrocannabinol (THC) (or analogues thereof) and cannabidiol (CBD) (or analogues thereof), it is preferred that the ratio by weight of THC:CBD is in the range of from 100:1 to 1:100, preferably 60:1 to 1:60.

When the formulation comprises tetrahydrocannabinol (THC) (or analogues thereof) and cannabidiol (CBD) (or analogues thereof), it is preferred that the ratio by weight of THC:CBD is in the range of from 20:1 to 1:20, more preferably 5:1 to 1:5. For example, the ratio of THC:CBD may be 1:1.

The unit dose of cannabinoid in the oral pharmaceutical formulation may be in the range of from 0.001 to 350 mg, preferably 0.1 to 350 mg, more preferably 1 to 250 mg.

For example, it is envisaged that, when in tablet or capsule unit dose form, the amount of cannabinoid present may be 0.5, 2, 10, 25, 50, 100, 150, 200, 250, 300 or 350 mg.

The amount of cannabinoid present in the formulation may be 20 to 30 wt %, based on the total composition. It has been found that the formulation is stable and is a solid at room temperature and pressure (defined herein as 20° C. and 1 atm) even when the content of cannabinoid is relatively high, such as 25, 30 or 35 wt %. Without wishing to be bound by theory, it is believed that at least one poloxamer is essential to the stability of the formulation, particularly for high cannabinoid content.

The Solvent

The formulation according to the present invention comprises a solvent, defined according to formula (I)

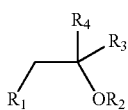

(I)

wherein $R_1$ and $R_2$ are independently selected from hydrogen, $C(O)CH_3$, OH, $C(O)CH_3$, $CH_2OH$ and $C(O)OCH_2CH_3$, $R_3$ is independently selected from $CH_3$, $CH_2OH$, OH, $CH_2OC(O)CH_3$ and $CH_2C(O)CH_2CH_3$; and $R_4$ is independently selected from hydrogen and $C(O)OCH_2CH_3$.

The solvent may be selected from the group consisting of diacetin, propylene glycol, triacetin, monoacetin, propylene glycol diacetate, triethyl citrate and mixtures thereof.

Diacetin is also known as glycerol diacetate.

Triacetin is also known as 1,2,3-triacetoxypropane, 1,2,3-triacetylglycerol or glycerol triacetate.

Monoacetin is also known as glycerol monoacetate or glycerol acetate.

Triethyl citrate is also known as citric acid ethyl ester.

Propylene glycol, propylene glycol diacetate and triethyl citrate are preferred solvents. Preferably, the solvent is triethyl citrate or propylene glycol. Triethyl citrate is preferably used.

The solvent may be present in an amount of from about 10 to 80 wt %, based on the total composition, preferably about 20 to 80 wt %, more preferably about 20 to 65 wt %, even more preferably about 20 to 50 wt %, most preferably about 20 to 30 wt %. The solvent may be present in an amount of about 25 wt %.

When the solvent used is diacetin, it is preferred that it is present in an amount of from about 20 to 50 wt %, based on the total composition.

When the solvent used is propylene glycol, it is preferred that it is present in an amount of from about 20 to 30 wt %, based on the total composition.

When the solvent is triacetin, it is preferred that it is present in an amount of from about 20 to 50 wt %, based on the total composition.

When the solvent is triethyl citrate, it is preferred that it is present in an amount of from about 20 to 50 wt %, based on the total composition, more preferably about 20 to 30 wt %.

When the solvent is propylene glycol diacetate, it is preferred that it is present in an amount of from about 20 to 50 wt %, based on the total composition.

When only one poloxamer is present, as will be described below, it is preferred that the solvent is present in an amount of from about 45 to 55 wt %, preferably 45 to 50 wt %, based on the total composition.

The solvent or mixture of solvents according to the claimed invention may be the only solvent in the formulation. For example, the formulation may be substantially water-free, substantially alcohol-free and/or substantially oil-free. By "substantially water-free", "substantially alcohol-free" and "substantially oil-free", it is meant that the formulation comprises less than 2 wt %, preferably less than 1 wt % water, alcohol and/or oil based on the total composition.

The formulation is preferably substantially free from ethanol. More preferably the formulation is substantially alcohol-free.

In some embodiments the formulation is used in a paediatric patient, i.e. a patient under 18 years of age. In paediatric patients, it may be preferred that the formulation is substantially alcohol-free.

The formulation may be substantially free from or comprise no triglycerides, diglycerides or monoglycerides or mixtures thereof derived from glycerol and at least one fatty acid selected from the group consisting of caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid and mixtures thereof. Preferably the formulation may be substantially free from or comprise no triglycerides, diglycerides or monoglycerides or mixtures thereof.

The formulation may be substantially free from hydrogenated vegetable oils, nut oils, anise oil, soybean oil, hydrogenated soybean oil, apricot kernel oil, corn oil, olive oil, peanut oil, almond oil, walnut oil, cashew oil, rice bran oil, poppy seed oil, cottonseed oil, canola oil, sesame oil, hydrogenated sesame oil, coconut oil, flaxseed oil, cinnamon oil, clove oil, nutmeg oil, coriander oil, lemon oil, orange oil, safflower oil, cocoa butter, palm oil, palm kernel oil, sunflower oil, rapeseed oil, castor oil, hydrogenated castor oil, polyoxyethylene castor oil derivatives, borage oil, beeswax, lanolin, petroleum jelly, mineral oil and light mineral oil.

More preferably the formulation may be free from triglycerides, diglycerides or monoglycerides or mixtures thereof derived from glycerol and caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid and mixtures thereof, hydrogenated vegetable oils, nut oils, anise oil, soybean oil, hydrogenated soybean oil, apricot kernel oil, corn oil, olive oil, peanut oil, almond oil, walnut oil, cashew oil, rice bran oil, poppy seed oil, cottonseed oil, canola oil, sesame oil, hydrogenated sesame oil, coconut oil, flaxseed oil, cinnamon oil, clove oil, nutmeg oil, coriander oil, lemon oil, orange oil, safflower oil, cocoa butter, palm oil, palm kernel oil, sunflower oil, rapeseed oil, castor oil, hydrogenated castor oil, polyoxyethylene castor oil derivatives, borage oil, beeswax, lanolin, petroleum jelly, mineral oil and light mineral oil.

Even more preferably the formulation may be oil-free.

The Poloxamer

The formulation according to the present invention comprises at least one poloxamer.

A poloxamer is defined according to formula (II)

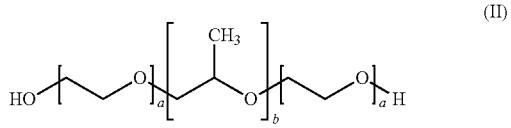

(II)

wherein a is an integer of from 10 to 110 and b is an integer of from 20 to 60.

It is preferred that when a is 12, b is 20. When a is 12 and b is 20, this is known as poloxamer 124.

It is also preferred that when a is 80, b is 27. When a is 80 and b is 27, this is known as poloxamer 188.

The formulation may comprise two poloxamers. When the formulation comprises two poloxamers, it is preferred that they are poloxamer 124 and poloxamer 188.

Other known poloxamers useful in the present invention are poloxamer 237 (a=64; and b=37), poloxamer 338 (a=141; and b=44) and poloxamer 407 (a=101; and b=56).

Further poloxamers that are known and can be useful in the present invention include poloxamer 108, poloxamer 182, poloxamer 183, poloxamer 212, poloxamer 217, poloxamer 238, poloxamer 288, poloxamer 331, poloxamer 338 and poloxamer 335.

The total amount of poloxamer present may be in an amount of from about 25 to 75 wt %, based on the total composition. Preferably the total amount of poloxamer present may be in the range of from about 25 to 60 wt % or 30 to 60 wt %, based on the total composition. More preferably the total amount of poloxamer present is from about 40 to about 50 wt %. The total amount of poloxamer present may be about 45 wt %.

When the formulation comprises poloxamer 124 and poloxamer 188, the amount of poloxamer 124 may be 5 wt % and the amount of poloxamer 188 may be 40 wt %, based on the total composition.

In some cases, the formulation may comprise only one poloxamer, wherein the poloxamer is poloxamer 188.

It has been found that, when poloxamer 407 is used, it is preferred that poloxamer 124 is present.

It has been found that the formulation of the invention has excellent rehydration properties. The formulation rehydrates rapidly and homogeneously. Upon rehydration the formulation has excellent release properties.

It has been found that the formulation of the invention has excellent stability. Without wishing to be bound by theory, it is believed that the presence of at least one poloxamer in the formulation affords excellent stability.

The Container (Pharmaceutical Package)

The pharmaceutical formulation according to the present invention is contained in a container (also referred to as "pharmaceutical package"). Preferably the container is a sealed container.

A container (pharmaceutical package) is a non-ingestible containment device which can hold the formulation of the invention. Examples of containers (pharmaceutical packages) include a sachet, a bottle, a tub, an ampoule, a blister pack, etc. Preferably the container is a bottle or a blister pack. Most preferably the container is a blister pack.

The container preferably protects the pharmaceutical formulation from moisture. Preferably the water content of the pharmaceutical formulation in the container increases by less than 5%, preferably less than 3%, more preferably less than 2% for a period of at least 1 year, preferably at least 2 years under ambient storage conditions, for example about 25° C. and 60% RH. The water content of the pharmaceutical formulation in the container may be measured according to ICH Guidance Q1A-Q1F.

Advantageously, whilst the formulation according to the present invention exhibits good storage stability when not contained in a container, i.e. as a stand-alone product, the storage stability can be further improved by containing the formulation in a container. For example, the increase in API degradants (such as CBE I, CBE II, OH-CBD and RRT 0.96) during storage can be decreased by containing the formulation in a container.

The container may be a bottle, for example a plastic, metal or glass bottle. Preferably the bottle is made from high-density polyethylene (HDPE), polyethylene terephthalate (PET), polypropylene (PP) or glass. Bottle packaging is known to those skilled in the art.

Most preferably the container (pharmaceutical package) is a blister pack. Blister packaging is known to those skilled in the art. A "blister pack" covers several types of pre-formed packaging used for consumer goods, food and pharmaceuticals. The term "blister pack" includes push-through, peel-push, tear-open, peelable and/or child-resistant blister packs. The basic configuration of a blister pack includes a forming film that has a plurality of cavities often referred to as "pockets" or "blisters" for holding a unit dosage form and a lidding material that provides the base component upon which the blister package is built. The lidding material is arranged on the face of the forming film that comprises the concave face of the at least one cavity. The lidding material is bonded, sealed or affixed to the forming film using a suitable method which is known in the art, such as by heat-sealing. The construction of the forming film and the lidding material varies. For example, one or both of the components may comprise a laminated structure that includes layers of various materials, such as paper, polymers and metals. Alternatively one or both of the components may comprise a single layer. The construction of the blister pack components determines its "barrier" properties against the environment, for example, against moisture, oxygen and/or light.

One type of forming film is a polyvinyl chloride (PVC) forming film. PVC is commonly used as a blister forming material within the pharmaceutical industry due to the low cost and facile formability of PVC. PVC as a forming material offers good protection of the pharmaceutical product in the blister pack against oxygen ingress but provides limited moisture protection. PVC forming films may be transparent or opaque. PVC forming films provide acceptable protection of pharmaceutical products but only limited protection of pharmaceutical products that are sensitive to moisture.

Another category of forming films are those comprising aluminium. When aluminium is used as a forming material it offers a substantially complete barrier to moisture and oxygen ingress. Surprisingly the inventors have discovered that these characteristics will lead to an extended shelf life of the formulation according to the present invention. Without wishing to be bound by theory, the reason behind the difference in barrier protection is due to the differing chemical compositions of the two materials. Permeation through aluminium is hindered because of the small interspaces between the molecules.

The blister pack may comprise a cavity forming film and a lidding material. The forming film may comprise at least one cavity.

The forming film and the lidding material may be made from different materials or may be made from the same material. The forming film may have a laminated structure or may be made from a single layer of material. The lidding material may be have a laminated structure or may be made from a single layer of material.

The forming film may comprise a polymer, paper, aluminium or combinations thereof. The polymer is preferably be selected from the group consisting of polyethylene (PE), polyvinyl chloride (PVC), polychlorotrifluoroethylene (PCTFE), polyvinylidene chloride (PVDC), high-density polyethylene (HDPE), polystyrene (PS), polypropylene (PP), polyethylene terephthalate (PET), polycarbonate or combinations thereof.

The forming film may comprise PVC, aluminium or combinations thereof.

Preferably the forming film is made from a laminated material comprising PVC and PVDC, more preferably PVC, PVDC and PE. When the forming film is made from a laminated material it is preferred that the lidding material comprises aluminium.

Preferably the forming film comprises aluminium. When the forming film comprises aluminium it is preferred that the lidding material comprises aluminium.

The lidding material may comprise a polymer, paper, aluminium or combinations thereof. The polymer may be selected from the group consisting of polyethylene (PE), polyvinyl chloride (PVC), polychlorotrifluoroethylene (PCTFE), polyvinylidene chloride (PVDC), high-density polyethylene (HDPE), polystyrene (PS), polypropylene (PP), polyethylene terephthalate (PET), polycarbonate or combinations thereof. Preferably the lidding material comprises aluminium.

Preferably both the forming film and the lidding material comprise aluminium.

Preferably the blister pack is a cold-form foil blister pack (also referred to as an "alu-alu" or an "aluminium/aluminium" or "Al/Al" blister pack).

Advantageously when the container is a blister pack, the formulation of the invention, for example in a unit dosage form, can be removed individually and thus without contamination of the other forms, which are furthermore contained in sealed cavities. In addition, the administration forms are separated from one another, preventing mutual interaction, such as, abrasion or sticking.

Advantageously when both the forming film and the lidding material comprise aluminium, the storage stability of the formulation according to the present invention is improved versus the formulation as a stand-alone product, and even better than when the formulation is stored in another type of container, e.g. one that does not comprise aluminium in both the forming film and the lidding material. Without wishing to be bound by theory, the inventors believe that this is because the permeability to moisture and oxygen is significantly reduced.

The container may contain a desiccant, for example a desiccant in a sachet or canister.

A desiccant is any drying agent that removes moisture from the air. Examples of a desiccant include activated carbon, calcium chloride, metal oxide, such as an alkaline earth metal oxide (such as calcium oxide), an alkaline earth metal hydroxide (such as calcium hydroxide), a sulfate of an alkaline earth metal (such as magnesium sulfate, calcium sulfate), silicon dioxide (silica gel), a bonded product of alumina oxide and silicon dioxide (silica alumina), alumina oxide (active alumina), natural or synthetic zeolite (molecular sieves 3A, 4A, SA, 13X), allophane, clay, a mixture of clay and activated carbon, a mixture of silica gel and activated carbon, a mixture of silica gel and clay, a mixture of silica alumina and activated carbon, a mixture of synthetic zeolite and activated carbon, a mixture of allophane and activated carbon (such as allophane added with activated carbon, or allophane kneaded with activated carbon), pulp containing silica gel (such as ultrafine silica gel mixed between paper fibers, silica gel packaged in paper tube), pulp containing calcium chloride (such as paper material impregnated with liquid calcium chloride, dried and coated with film) and pulp containing allophane (such as pulp impregnated with allophane liquid, dried and film coated, allophane packaged in paper tube).

Preferably the desiccant is selected from the group consisting of silica gel, clay desiccants, calcium sulfate, calcium chloride, calcium oxide, zeolite, activated alumina, activated carbon, alumina, bauxite, anhydrous calcium sulphate, activated bentonite clay, water-absorbing clay, molecular sieve and combinations thereof. More preferably the desiccant is selected from the group consisting of silica gel, clay desiccants, calcium sulfate, calcium chloride, calcium oxide, zeolite, activated alumina, activated carbon and combinations thereof.

When the container is a bottle, the container preferably contains a desiccant.

The container may contain an oxygen absorber.

Oxygen absorbers absorb and remove oxygen from the air. Examples of an oxygen absorber include metal-based substances that remove oxygen by reacting with it by chemical bonding, generally forming a metal oxide component. Metal-based substances include elemental iron as well as iron oxide, iron hydroxide, iron carbide and the like. Other metals for use as oxygen absorbers include nickel, tin, copper and zinc. Additional materials for oxygen absorbers include low molecular weight organic compounds such as ascorbic acid, sodium ascorbate, catechol and phenol; and polymeric materials incorporating a resin and a catalyst.

Antioxidant

The formulation may further comprise an antioxidant, preferably in an amount of from about 0.001 to 5 wt %, more preferably about 0.001 to 2.5 wt %, based on the total composition.

The antioxidant may be selected from the group consisting of butylated hydroxytoluene, butylated hydroxyl anisole, alpha-tocopherol (Vitamin E), ascorbyl palmitate, ascorbic acid, sodium ascorbate, ethylenediamino tetraacetic acid, cysteine hydrochloride, citric acid, sodium citrate, sodium bisulfate, sodium metabisulfite, lecithin, propyl gallate, sodium sulfate, monothioglycerol and mixtures thereof.

A preferred group of antioxidants is alpha-tocopherol (Vitamin E), monothioglycerol, ascorbic acid, citric acid and mixtures thereof. A preferred antioxidant is alpha-tocopherol (Vitamin E).

Advantageously when the formulation comprises an antioxidant the stability of the formulation can be improved further still.

Additional Agents

The formulation may additionally comprise a flavouring agent, such as peppermint.

The formulation may additionally comprise a sweetener, such as sucrose.

Forms

The formulation according to the invention may be in an oral dosage form selected from the group consisting of mucoadhesive gel, a tablet, a powder, a liquid gel capsule, a solid capsule, an oral solution, granule or extrudates. A preferred group of oral dosage forms is the group consisting of a gel capsule and a solid capsule.

The oral dosage form preferably comprises a modified-release agent.

The modified-release agent may be selected from the group consisting of polymethacrylate derivatives, hypromellose derivatives, polyvinylacetate derivatives, poluvinylether derivatives, cellulose derivatives, shellac, gellan gum, zein, alginic acid and waxes.

The modified-release agent may be selected from the group consisting of polymethacrylate derivatives (such as a copolymer of methacrylic acid and methacrylate, a copolymer of methacrylic acid and methyl methacrylate or a copolymer of methacrylic acid and ethylacrylate); hypromellose derivatives (such as hydroxypropyl methyl cellulose acetate succinate (HPMC-AS) and hydroxypropyl methyl cellulose phthalate (HPMCP)); polyvinylacetate derivatives (such as polyvinyl acetate phthalate (PVAP)); polyvinylether derivatives (such as a copolymer of methyl vinyl ether and maleic anhydride); cellulose derivatives (such as cellulose acetate phthalate (CAP), cellulose acetate terephthalate, cellulose acetate isophthalate, cellulose acetate butyrate (CAB), cellulose acetate trimellitate (CAT), cellulose acetate succinate (CAS), ethyl cellulose, methyl cellulose); shellac, gellan gum, zein, alginic acid, waxes and mixtures thereof.

The modified-release agent may be selected from the group consisting of a copolymer of methacrylic acid and methacrylate, a copolymer of methacrylic acid and methyl methacrylate, a copolymer of methacrylic acid and ethylacrylate, hydroxypropyl methyl cellulose acetate succinate (HPMC-AS), hydroxypropyl methyl cellulose phthalate (HPMCP), polyvinyl acetate phthalate (PVAP), a copolymer of methyl vinyl ether and maleic anhydride, cellulose acetate phthalate (CAP), cellulose acetate butyrate (CAB), cellulose acetate trimellitate (CAT), cellulose acetate succinate (CAS), ethyl cellulose, methyl cellulose, shellac, gellan gum, zein, alginic acid and waxes.

The modified-release agent may be an acid-resistant agent.

The modified-release agent may be an enteric agent.

A preferred group of oral dosage forms is the group consisting of a gel capsule and a solid capsule. When the oral pharmaceutical composition is in the dosage form of a capsule, the pharmaceutical formulation is contained in the capsule and the capsule comprises the modified-release agent (either as part of the capsule material, or the capsule comprises a coating which comprises the modified-release agent).

The capsule may comprise the modified-release agent as part of the capsule material, for example a capsule which is made from a material that comprises a modified-release agent.

The capsule may be coated with a coating comprising the modified-release agent, for example a capsule which is not made from a material that comprises a modified-release agent, but which is coated with a coating that comprises the modified-release agent.

The oral dosage form may be a capsule which comprises a modified-release agent, for example a capsule which is made from a material that comprises a modified-release agent, and which is coated with a coating that comprises the modified-release agent.

The oral dosage form may be an acid-resistant dosage form.

The oral dosage form may be an enteric dosage form, such as an enteric capsule.

The pharmaceutical formulation according to the present invention may be filled into capsules with a modified-release coating, wherein the coating comprises at least one a modified-release agent.

The pharmaceutical formulation according to the present invention may be filled into modified-release capsules which comprise the least one modified-release agent as part of the capsule material.

Preferably the modified-release capsule comprises a modified hydroxypropyl methyl cellulose (HPMC) (also termed "hydroxypropyl methyl cellulose derivative" and "hypromellose derivative"). For example, the modified-release capsule may be a capsule comprising hydroxypropyl methyl cellulose acetate succinate (HPMC-AS).

Preferably the modified-release capsule comprises a coating comprising cellulose acetate phthalate (CAP).

Preferred Formulations

It is preferred that the type IV oral formulation according to the invention is a solid at room temperature and pressure, i.e. preferably the formulation is a solid at 20° C. and 1 atm. Such formulations are typically fluid during manufacture, solid at room temperature and become fluid again at 37° C. For the purposes of the invention, a gel is considered to be a solid.

The formulation may comprise about 20 to 65% solvent and about 25 to 75 wt % poloxamer, based on the pharmaceutical formulation.

The formulation may comprise about 20 to 50 wt % solvent and two poloxamers, wherein the total amount of poloxamer is about 25 to 60 wt %, based on the pharmaceutical formulation.

The formulation may comprise about 20 to 30 wt % solvent and two poloxamers, wherein the total amount of poloxamer is about 30 to 60 wt %, based on the pharmaceutical formulation.

Preferably the formulation comprises about 20 to 30 wt % cannabinoid, about 20 to 30 wt % solvent and two poloxamers, wherein the total amount of poloxamer is about 30 to 60 wt %, based on the pharmaceutical formulation.

Preferably the formulation comprises at least one cannabinoid, wherein the cannabinoid is CBD; at least two poloxamers, wherein the poloxamers are poloxamer 124 and poloxamer 188; and a solvent, wherein the solvent is triethyl citrate. More preferably the formulation comprises about 20 to 30 wt % CBD; about 20 to 30 wt % triethyl citrate; and two poloxamers, wherein the poloxamers are poloxamer 124 and poloxamer 188, wherein the total amount of poloxamer is about 30 to 60 wt %, based on the pharmaceutical formulation.

In a highly preferred formulation, the formulation comprises about 20 to 30 wt % CBD; about 20 to 30 wt % triethyl citrate; an anti-oxidant, wherein the antioxidant is alpha-tocopherol; and two poloxamers, wherein the poloxamers are poloxamer 124 and poloxamer 188, wherein the total amount of poloxamer is about 40 to 50 wt %, based on the pharmaceutical formulation. In this preferred formulation, the formulation is in the form of an oral dosage form, wherein the oral dosage form is a capsule; and the capsule comprises a modified-release agent. In this preferred formulation, the oral dosage form is contained in a blister pack.

Preferably the formulation consists of at least one cannabinoid; at least one poloxamer; a solvent; and optionally an antioxidant, wherein the solvent is defined according to formula (I)

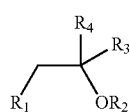
(I)

wherein $R_1$ and $R_2$ are independently selected from hydrogen, $C(O)CH_3$, OH, $C(O)CH_3$, $CH_2OH$ and $C(O)OCH_2CH_3$; $R_3$ is independently selected from $CH_3$, $CH_2OH$, OH, $CH_2OC(O)CH_3$ and $CH_2C(O)CH_2CH_3$; and $R_4$ is independently selected from hydrogen and $C(O)OCH_2CH_3$.

The following represent preferred formulations according to the invention that are capable of forming a gel at body temperature.

A preferred oral pharmaceutical formulation (solid gel at room temperature) comprises
 25 wt % cannabidiol;
 34 wt % poloxamer 124;
 15 wt % poloxamer 188; and
 26 wt % propylene glycol.

A further preferred oral pharmaceutical formulation (Gel at room temperature) comprises
 25 wt % cannabidiol;
 34 wt % poloxamer 124;
 15 wt % poloxamer 188; and
 26 wt % diacetin.

A further preferred oral pharmaceutical formulation (Semi-solid gel at room temperature) comprises
 25 wt % cannabidiol;
 25 wt % poloxamer 124;
 25 wt % poloxamer 407; and
 25 wt % propylene glycol.

A further preferred oral pharmaceutical formulation (Solid at room temperature) comprises
 25 wt % cannabidiol;
 35 wt % poloxamer 124;
 20 wt % poloxamer 188; and
 20 wt % propylene glycol.

A further preferred oral pharmaceutical formulation (Gel at room temperature) comprises
 35 wt % cannabidiol;
 28 wt % poloxamer 124;
 16 wt % poloxamer 188; and
 22 wt % propylene glycol.

A further preferred oral pharmaceutical formulation (Solid at room temperature) comprises
 12.5 wt % cannabidiol;
 38 wt % poloxamer 124;
 19 wt % poloxamer 188; and
 30 wt % propylene glycol.

A further preferred oral pharmaceutical formulation (Gel at room temperature) comprises
 25 wt % cannabidiol;
 27 wt % poloxamer 188; and
 48 wt % diacetin.

A further preferred oral pharmaceutical formulation (Gel at room temperature) comprises
 30 wt % cannabidiol;
 27 wt % poloxamer 188; and
 43 wt % diacetin.

A further preferred oral pharmaceutical formulation (Gel at room temperature) comprises
 25 wt % cannabidiol;
 27 wt % poloxamer 188; and
 48 wt % triacetin.

A further preferred oral pharmaceutical formulation (Semi-solid gel at room temperature) comprises
 25 wt % cannabidiol;
 27 wt % poloxamer 188; and
 48 wt % propylene glycol.

A further preferred oral pharmaceutical formulation (Solid at room temperature) comprises
 25 wt % cannabidiol;
 35 wt % poloxamer 124;
 20 wt % poloxamer 188; and
 20 wt % triethyl citrate.

A further preferred oral pharmaceutical formulation (Gel at room temperature) comprises
 25 wt % cannabidiol;
 27 wt % poloxamer 188; and
 48 wt % triethyl citrate.

A further preferred oral pharmaceutical formulation (Gel at room temperature) comprises
 25 wt % cannabidivarin;
 27 wt % poloxamer 188; and
 48 wt % triethyl citrate.

A further preferred oral pharmaceutical formulation (Solid at room temperature) comprises
  25 wt % cannabidivarin;
  35 wt % poloxamer 124;
  20 wt % poloxamer 188; and
  20 wt % propylene glycol.

A further preferred oral pharmaceutical formulation (Solid at room temperature) comprises
  20 wt % cannabidivarin;
  35 wt % poloxamer 124;
  25 wt % poloxamer 188; and
  20 wt % triacetin.

A further preferred oral pharmaceutical formulation (Solid at room temperature) comprises
  25 wt % cannabidivarin;
  35 wt % poloxamer 124;
  20 wt % poloxamer 188; and
  20 wt % triethyl citrate.

Treatment

The formulation is for use in therapy, preferably for use in paediatric epilepsy.

The formulation may also be used in the treatment of a disease or disorder selected from the group consisting of Dravet Syndrome, Lennox Gastaut Syndrome, myocolonic seizures, juvenile myocolonic epilepsy, refractory epilepsy, schizophrenia, juvenile spasms, West syndrome, infantile spasms, refractory infantile spasms, tuberous sclerosis complex, brain tumors, neuropathic pain, cannabis use disorder, post-traumatic stress disorder, anxiety, early psychosis, Alzheimer's Disease, and autism.

As already stated, cannabidiol is preferred for use in the present invention. Cannabidiol can be used in the treatment of atonic, absence or partial seizures, in particular, simple or complex seizures. It is particularly effective in reducing seizures in patients suffering with etiologies that include: Lennox-Gastaut Syndrome; Tuberous Sclerosis Complex; Dravet Syndrome; Doose Syndrome; CDKL5; Dup15q; Jeavons syndrome; Myoclonic Absence Epilepsy; Neuronal ceroid lipofuscinoses (NCL) and brain abnormalities.

In addition, a formulation comprising CBDV and/or CBDA can be used in the treatment of autism spectrum disorders, in particular Rett syndrome, Fragile X syndrome, Angelman syndrome, ADHD and hyperkinetic disorders, such as Tourette syndrome and dystonias. Thus, the formulation comprising CBDV and/or CBDA can be useful in a method of treatment of such disorders.

The formulation of the invention may be useful in a method of treating a patient having a disorder selected from the group consisting of Dravet Syndrome, Lennox Gastaut Syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumors, neuropathic pain, cannabis use disorder, post-traumatic stress disorder, anxiety, early psychosis, Alzheimer's Disease, and autism.

When cannabidiol is used in the formulation, the formulation may be useful in a method of treatment of atonic, absence or partial seizures in a patient, in particular, simple or complex seizures. It is particularly effective in a method of reducing seizures in patients suffering with etiologies that include: Lennox-Gastaut Syndrome; Tuberous Sclerosis Complex; Dravet Syndrome; Doose Syndrome; CDKL5; Dup15q; Jeavons syndrome; Myoclonic Absence Epilepsy; Neuronal ceroid lipofuscinoses (NCL) and brain abnormalities.

The method of treatments comprise administering a patient with a therapeutically effective amount of a formulation or of a cannabinoid in a formulation according to the present invention.

Definitions

"Cannabinoids" are a group of compounds including the endocannabinoids, the phytocannabinoids and those which are neither endocannabinoids nor phytocannabinoids, hereinafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the cannabis plant. Examples include WIN 55212 and rimonabant.

An "isolated phytocannabinoid" is one which has been extracted from the cannabis plant and purified to such an extent that all the additional components such as secondary and minor cannabinoids and the non-cannabinoid fraction have been removed.

A "synthetic cannabinoid" is one which has been produced by chemical synthesis. This term includes modifying an isolated phytocannabinoid, by, for example, forming a pharmaceutically acceptable salt thereof.

A "substantially pure" cannabinoid is defined as a cannabinoid which is present at greater than 95% (w/w) pure. More preferably greater than 96% (w/w) through 97% (w/w) thorough 98% (w/w) to 99% % (w/w) and greater.

A "highly purified" cannabinoid is defined as a cannabinoid that has been extracted from the cannabis plant and purified to the extent that other cannabinoids and non-cannabinoid components that are co-extracted with the cannabinoids have been substantially removed, such that the highly purified cannabinoid is greater than or equal to 95% (w/w) pure.

A "botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes."

A botanical drug substance does not include a highly purified or chemically modified substance derived from natural sources. Thus, in the case of cannabis, BDS derived from cannabis plants do not include highly purified Pharmacopoeial grade cannabinoids.

An "oil" is typically defined as a single compound or a mixture of compounds that are both hydrophobic and lipophilic. Exemplary oils include triglycerides, diglycerides, monoglycerides, fatty acids and fatty acid esters. Triglycerides, diglycerides and monoglycerides are esters derived from glycerol and three, two or one fatty acids. Diglycerides and triglycerides may have the same or they may have different fatty acids for each ester bond. Exemplary fatty acids include carboxylic acids with a saturated or unsaturated, linear or branched carbon chains, such as caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid. Exemplary mixtures of oils include plant and animal fats and waxes such as vegetable oils, hydrogenated vegetable oils, nut oils, anise oil, soybean oil, hydrogenated soybean oil, apricot kernel oil, corn oil, olive oil, peanut oil, almond oil, walnut oil, cashew oil, rice bran oil, poppy seed oil, cottonseed oil, canola oil, sesame oil, hydrogenated sesame oil, coconut oil, flaxseed oil, cinnamon oil, clove oil, nutmeg oil, coriander oil, lemon oil, orange oil, safflower oil, cocoa butter, palm oil, palm kernel oil, sunflower oil, rapeseed oil, castor oil, hydrogenated castor oil, polyoxyethylene castor oil derivatives, borage oil, beeswax, lanolin, petroleum jelly, mineral oil and light mineral oil. For the purposes of the present invention cannabinoids are not considered to be oils.

An "alcohol" has its standard meaning within the art. It includes ethanol, propanol etc.

"Room temperature and pressure" is defined herein as 20° C. and 1 atm.

"Modified-release" as used herein refers to the process and result of modifying an oral dosage form to release a drug with a delay after its oral administration, or for a prolonged period of time, or to a specific target. For the purposes of the present invention, hydroxypropyl methyl cellulose (HPMC) is not considered a modified-release agent.

"Acid-resistant" or "acid resistance" as used herein means that the oral dosage form does not dissolve (or disintegrate) substantively in solutions with a pH of less than 5, preferably less than 4, more preferably less than 3, even more preferably less than 2; but does dissolve in solutions with a pH of more than 5. For example, the oral dosage form may not dissolve in gastric acid.

The term "enteric" means that the oral dosage form does not dissolve (or disintegrate) substantively in gastric acid (either in the fed or fasted state) or in the stomach but does dissolve in the intestines (small intestine, large intestine). For example, the oral dosage form may dissolve substantively in the jejunum or colon, etc.

Examples

1. Analytical Procedures, Cannabinoids and Excipients Used in the Examples

1.1. Rehydration (RH) Procedure

A type IV oral pharmaceutical formulation (OPF) comprising at least one cannabinoid, at least one solvent and at least one poloxamer was rehydrated by adding 20 mL water for injections at room temperature (RH-RT) or by adding 20 mL water for injections at 37° C. (RH-37) in Class-3 glass colourless transparent vials. The vials were vortexed for 10 seconds.

1.2. Test for Appearances of OPF

The viscosity, homogeneity and clarity of the OPF was checked visually.

1.3. Appearance of Rehydrated OPF

After rehydration, the formulation is checked visually on homogeneity and presence of particles and/or non-rehydrated OPF. The presence of foam is an indication that enough poloxamer is used to rehydrate the cannabinoid(s).

1.4. Release of Cannabinoid in Rehydration Fluid

The release of cannabinoid in the rehydration fluid was tested as follows: Rehydrated OPF was submitted for HPLC analysis. Equipment: HPLC system with variable wavelength UV detector or diode array detector. Column: Ace C18-AR 150×4.6 mm, 3 μm. Pre-Column: Ace C18-AR Guard Cartridge. Mobile Phase: Acetonitrile: 0.25% acetic acid (62%:38%). Column Temperature: 38° C. Flow Rate: 1.0 ml min-1. Detection: 220 nm. Injection Volume: 10 μl. Run Time 25 minutes. Sample preparation: accurately prepare test samples at an approximate concentration of 0.15 mg/ml in triplicate. Samples may be prepared at a higher concentration to ensure accurate quantification of related substances or degradants. 0.1 mL rehydrated OPF was diluted with 10 mL ethanol; 10 μL was injected into the HPLC system.

1.5. Cannabinoids

CBD: synthetic, plant derived CBD containing waxes and plant derived recrystallized CBD (CBD-r). Plant derived CBDV and synthetic CBDV.

1.6. Excipients

Lutrol L44 (BASF, poloxamer 124: P124), Lutrol F68 (BASF, poloxamer 188: P188), Lutrol F87 (BASF, poloxamer 237: P237), Lutrol F108 (BASF, poloxamer 338: P338), Lutrol F127 (BASF, poloxamer 407, P407), glycerol (Sigma: gly), diacetin (Sigma: di), triacetin (Sigma: tri), propylene glycol (Sigma: PG), ethanol (Fischer), propylene glycol diacetate (Sigma: PGDA), triethyl citrate (Sigma: TEC).

1.7. Melt Procedure

Unless otherwise stated all formulations were produced using the following method. The excipients and cannabinoids are weighed into a vessel and are heated until molten. Upon cooling the gel is filled into capsules or vials by weight. The viscosity of the gel is a function of temperature which enables the flexibility of filling into HPMC, Gelatin and soft-Gelatin capsules.

Alternatively, gel based formulations can be manufactured where the excipients and cannabinoids can be dissolved into an organic solvent such as, ethanol, methanol, propanol and filled into glass vials with a process step of evaporating the organic solvent off to leave the gel in the vial.

2. Stability

Stability of the formulation as a stand-alone product was measured as well as the stability of the formulation stored in a container according to the invention. The stability studies demonstrate that the stand-alone product has good storage stability, but the stability is improved when the product is stored in a container and further improved when the container is a blister pack with a forming film and a lidding material that both comprise aluminium (Alu/Alu blister packs).

3. Stand-Alone Stability

Stability of OPF was executed according to ICH Guidance Q1A-Q1F. Samples were stored at 25° C.±2° C./60%

RH±5%, 30° C.±2° C./65% RH±5% RH and 40° C.±2° C./75% RH±5%. Stability of OPF was assessed by chemical analysis and appearance described above. Chemical analysis was performed by a stability indicating HPLC method, described above. The number of repeat experiments for each time point was 3, except at 6 months, when 6 repeat experiments were conducted. Sample preparation: 0.1 mL rehydrated OPF was diluted with 10 mL ethanol; 10 μL was injected into the HPLC system.

The following formulation was prepared for use in the stand-alone stability study.

Type IV formulation (150 mg/capsule): 30% w/w CBD; 5% w/w P124; 40% w/w P188; and 25% w/w triethyl citrate.

The purpose of stability testing is to provide evidence on how the quality of a drug product varies with time under the influence of a variety of environmental factors such as temperature and humidity. In order to illustrate that the Type IV formulations according to the invention exhibit excellent stability, stability of OPF was executed according to ICH Guidance Q1A-Q1F.

The results of the stability study are represented in Tables 1-3 below. Table 1 presents the data for samples stored at 25° C.±2° C./60% RH±5%. Table 2 presents the data for samples stored at 30° C.±2° C./65% RH±5% RH. Table 3 presents the data for samples stored at 40° C.±2° C./75% RH±5%.

TABLE 1

| | Time Point (Months) | | | |
|---|---|---|---|---|
| | 0 | 3 | 6 | 7 |
| CBD Content (mg/Capsule) | 149.13 | 149.56 | 149.54 | 147.70 |
| (% of Initial CBD Content) | 100.00 | 100.3 | 100.3 | 99.0 |

TABLE 2

| | Time Point (Months) | | | |
|---|---|---|---|---|
| | 0 | 3 | 6 | 7 |
| CBD Content (mg/Capsule) | 149.13 | 150.12 | 148.58 | 147.05 |
| (% of Initial CBD Content) | 100.00 | 100.7 | 99.6 | 98.6 |

TABLE 3

| | Time Point (Months) | | |
|---|---|---|---|
| | 0 | 3 | 6 |
| CBD Content (mg/Capsule) | 149.13 | 148.02 | 146.20 |
| (% of Initial CBD Content) | 100.00 | 99.3 | 98.0 |

As shown in Tables 1-3, the Type IV formulations according to the invention exhibit excellent stability, even under strenuous conditions, such as 40° C.±2° C./75% RH±5%. Even under storage conditions of 40° C.±2° C./75% RH±5%, 98% of the initial CBD content was recovered after 6 months.

In summary, it has been shown that a Type IV formulation according to the invention, exhibits excellent stability.

4. Stability in a Container

The purpose of stability testing is to provide evidence on how the quality of a drug product varies with time under the influence of a variety of environmental factors such as temperature and humidity. In order to illustrate that the formulations contained in a container according to the invention exhibit excellent stability, stability was tested.

Three sample sets were evaluated in the study. The following formulations were prepared for use in the stability in container study.

Sample 1 (150 mg/capsule): 30% w/w CBD; 5% w/w P124; 40% w/w P188; and 25% w/w triethyl citrate. Capsules were contained in PVC blister packs.

Sample 2 (150 mg/capsule): 30% w/w CBD; 5% w/w P124; 39.9% w/w P188; 25% w/w triethyl citrate, and 0.1% alpha-tocopherol. Capsules were contained in PVC blister packs.

Sample 3 (150 mg/capsule): 30% w/w CBD; 5% w/w P124; 39.9% w/w P188; 25% w/w triethyl citrate, and 0.1% alpha-tocopherol. Capsules were contained in alu-alu blister packs.

Stability was evaluated according to ICH Guidance Q1A-Q1F. The samples were stored at 40° C.±2° C./75% RH±5%, which are the conditions for accelerated study and are highly demanding. Stability of OPF was assessed by chemical analysis and appearance described above. Chemical analysis was performed by a stability indicating HPLC method, described above. The number of repeat experiments for each time point was 3. Sample preparation: 0.1 mL rehydrated OPF was diluted with 10 mL ethanol; 10 μL was injected into the HPLC system. The amounts of CBE I, CBE II, OH-CBD and RRT 0.96 were measured in aliquots taken at 0, 3, 9, 12 and 24 weeks.

The results of the study are presented in Table 4 below.

TABLE 4

| Time Point (weeks) | CBE I + CBE II (%) | | | RRT 0.96 (%) | | | OH-CBD (%) | | |
|---|---|---|---|---|---|---|---|---|---|
| | Sample 1 | Sample 2 | Sample 3 | Sample 1 | Sample 2 | Sample 3 | Sample 1 | Sample 2 | Sample 3 |
| 0 | ND | ND | ND | ND | ND | ND | ND | ND | ND |
| 3 | — | 0.04 | 0.03 | — | 0.05 | 0.05 | — | <BLQ 0.05 | <BLQ 0.05 |
| 9 | — | 0.15 | 0.09 | — | 0.13 | 0.06 | — | <BLQ 0.05 | <BLQ 0.05 |

TABLE 4-continued

| Time Point | CBE I + CBE II (%) | | | RRT 0.96 (%) | | | OH-CBD (%) | | |
|---|---|---|---|---|---|---|---|---|---|
| (weeks) | Sample 1 | Sample 2 | Sample 3 | Sample 1 | Sample 2 | Sample 3 | Sample 1 | Sample 2 | Sample 3 |
| 12 | 0.54 | 0.20 | 0.10 | 0.29 | 0.17 | 0.05 | 0.04 | <BLQ 0.05 | <BLQ 0.05 |
| 24 | 1.13 | 0.53 | 0.10 | 0.39 | 0.28 | 0.03 | 0.02 | <BLQ 0.05 | <BLQ 0.05 |

ND means that the compound was not detected.
<BLQ 0.05 means that the compound was detected in an amount below the level of quantification. In this study the level of quantification was 0.05%.

The weight of the formulations contained in a container according to the invention was also measured after storage at 40° C.±2° C./75% RH±5% for 24 weeks. The increase in capsule weight is indicative of moisture ingress. The results are presented in Table 5 below and are expressed as a percentage increase in capsule weight at 24 weeks versus the capsule weight at week 0.

TABLE 5

| | Sample 1 | Sample 2 | Sample 3 |
|---|---|---|---|
| Increase in capsule weight/% | 2.90 | 3.14 | 0.07 |

5. Bioavailability

In order to illustrate that the Type IV formulations according to the invention exhibit improved bioavailability relative to Type I and Type III formulations, a comparison was made and bioavailability for each formulation measured. The results of the bioavailability study are represented in Table 6 below.

The outcome of the study is also depicted in The FIGURE. As can be seen, the Type IV formulation, according to the present invention exhibits improved bioavailability compared to Type I and Type III formulations having the same concentration of CBD. As shown in Table 4, the result of subject 50 appears to be an anomaly because it falls outside of the general trend of improved bioavailability. This is clearly shown in The FIGURE, despite inclusion of the anomaly.

In summary, it has been shown that a Type IV formulation, as classified by the Lipid Formulation Classification System, exhibits improved bioavailability for CBD.

5.1. Details of the PK Study for Measurement of Bioavailability

Beagle dogs (supplied by Charles River UK) received oral capsule doses at a target level of 15 mg/kg. Capsules used were size '0' gelatine capsules and the animals received a 100 mL water flush after each capsule was administered.

The volume of blood taken at each sampling time was 2 mL and were collected mostly from the jugular vein. On a few occasions, cephalic vein samples were collected. The sampling times were: 0.5, 1, 1.5, 2, 2.5, 3, 4, 5, 6, 8, 12 and 24 h post-dose. The determination of CBD, 6-OH CBD, THC and 11 OH THC in dog plasma was performed by protein precipitation with reverse phase liquid chromatography with tandem mass spectrometric detection. The LLOQ of CBD was 1 ng/ml and all metabolites had an LLOQ of 0.5 ng/ml.

The human equivalent dose (HED) can be estimated using the following formula:

$$HED = \frac{\text{Animal dose (mg/kg) multiplied by Animal } K_m}{\text{Human } K_m}$$

The $K_m$ for a dog is 20 and the $K_m$ for a human is 37. Thus, for a human a 15 mg/kg dose in a dog equates to a human dose of about 8.1 mg/kg.

5.2. Formulations for Measurement of Bioavailability

Diacetin was weighed by weight into a vial followed by P124 directly on top. The P188 was weighed and added to the vessel containing the diacetin and P124. Finally, the desired amount of CBD is weighed and added to the vessel and heated (100° C.) until molten with a vortex to ensure a homogenous gel. Upon cooling (30-40° C.) the gel is filled into capsules or vials by weight. The viscosity of the gel is a function of temperature which enables the flexibility of filling into HPMC, Gelatin and soft-Gelatin capsules. At room temperature, low CBD dose gels were solid whereas the higher loaded CBD formulations remained a gel.

The following formulations were prepared for use in the PK study.

Type IV Gel (125 mg/g): 12.5% w/w CBD; 38% w/w P124; 19% w/w P188; and 30% w/w diacetin. Release=99.3%. Appearance=solid gel.

Type IV Gel (250 mg/g): 25% w/w CBD; 34% w/w P124; 15% w/w P188; and 26% w/w diacetin. Release=97.4%. Appearance=clear gel.

In both gel formulations, the CBD used was a highly purified form.

Type II I(i) SEDDS (250 mg/g): CBD formulated with 15 wt % oil, 45 wt % water soluble surfactants and 40 wt % hydrophilic cosolvent.

Type III(ii) SEDDS (250 mg/g): CBD formulated with 31 wt % oil, 45 wt % water soluble surfactants and 24 wt % hydrophilic cosolvent.

TABLE 6

Estimated bioavailabilities based on AUC(0-t) data for CBD

| Analyte | Oral Formulation | Subject 47 | 48 | 49 | 50 | 57 | 58 | 59 | 60 | 61 | 62 | 63 | N | Mean | SD |
|---|---|---|---|---|---|---|---|---|---|---|---|---|---|---|---|
| | | | | | | Bioavailability_using_AUCt_for_CBD | | | | | | | | | |
| Type I | Control Oil based (125 mg/g) | 4.43 | 2.95 | | | 2.11 | 1.67 | 2.43 | | | | | 5 | 2.72 | 1.07 |
| Type III(i) | SEDDS (250 mg/g) | 19.9 | 46.7 | | | 15.5 | 20.0 | 27.0 | | | | | 5 | 25.8 | 12.4 |
| Type III(ii) | SEDDS (250 mg/g) | | | 9.00 | 11.7 | 14.6 | | | | 6.62 | 6.65 | 16.3 | 6 | 10.8 | 4.09 |
| Type IV | Gel (125 mg/g) | | | 20.4 | | 31.1 | | | | 10.3 | 25.9 | 22.3 | 5 | 22.0 | 7.70 |
| Type IV | Gel (250 mg/g) | | | 37.2 | 17.3 | 38.0 | | | | 55.7 | 53.5 | 44.3 | 6 | 41.0 | 13.9 |

The invention claimed is:

1. An oral pharmaceutical formulation comprising:
cannabidiol (CBD) or cannabidivarin (CBDV);
poloxamer 124 or poloxamer 188, or a mixture thereof; and
diacetin, propylene glycol, triacetin, monoacetin, propylene glycol diacetate, triethyl citrate, or a mixture thereof;
wherein the oral pharmaceutical formulation is contained in a container,
wherein the container is a blister pack, and
wherein the blister pack comprises a cavity forming film comprising aluminium and a lidding material comprising aluminium.

2. The formulation according to claim 1, wherein the poloxamer 124 or poloxamer 188, or the mixture thereof is present in an amount of from about 25 to 75 wt %, based on the total composition.

3. The formulation according to claim 1, which comprises propylene glycol, propylene glycol diacetate, triethyl citrate, or a mixture thereof.

4. The formulation according to claim 1, which comprises propylene glycol, triethyl citrate, or a mixture thereof.

5. The formulation according to claim 1, which comprises triethyl citrate.

6. The formulation according to claim 1, wherein the diacetin, propylene glycol, triacetin, monoacetin, propylene glycol diacetate, triethyl citrate, or the mixture thereof is present in an amount of from about 10 to 80 wt %, based on the total composition.

7. The formulation according to claim 1, wherein the cannabidiol (CBD) or cannabidivarin (CBDV) is present in an amount of from about 10 to 50 wt %, based on the total composition.

8. The formulation according to claim 1, further comprising an antioxidant.

9. The formulation according to claim 8, wherein the antioxidant comprises butylated hydroxyltoluene, butylated hydroxyl anisole, alpha- tocopherol (Vitamin E), ascorbyl palmitate, ascorbic acid, sodium ascorbate, ethylenediamino tetraacetic acid, cysteine hydrochloride, citric acid, sodium citrate, sodium bisulfate, sodium metabisulfite, lecithin, propyl gallate, sodium sulfate, monothioglycerol, or a mixture thereof.

10. The formulation according to claim 9, wherein the antioxidant comprises alpha-tocopherol (Vitamin E), monothioglycerol, ascorbic acid, citric acid, or a mixture thereof.

11. The formulation according to claim 1, wherein the formulation is substantially oil-free.

12. The formulation according to claim 1, wherein the formulation is a solid at 20° C. and 1 atm.

13. The formulation according to claim 1, wherein the container comprises a desiccant.

14. The formulation according to claim 13, wherein the desiccant comprises silica gel, a clay desiccant, calcium sulfate, calcium chloride, calcium oxide, zeolite, activated alumina, activated charcoal, alumina, bauxite, anhydrous calcium sulphate, activated bentonite clay, water-absorbing clay, molecular sieve, or a combination thereof.

15. The formulation according to claim 1, wherein the formulation is a mucoadhesive gel, a tablet, a powder, a liquid gel capsule, a solid capsule, an oral solution, a granule, or an extrudate.

16. The formulation according to claim 15, wherein the formulation comprises a modified-release agent.

17. The formulation according to claim 1, wherein the blister pack is a cold-form foil blister pack.

18. The formulation according to claim 1, wherein the cavity forming film comprises a laminated material.

* * * * *